(12) United States Patent
Hall et al.

(10) Patent No.: US 11,026,704 B2
(45) Date of Patent: Jun. 8, 2021

(54) VASCULAR ACCESS ASSEMBLY DECLOTTING SYSTEMS AND METHODS

(71) Applicant: Merit Medical Systems, Inc., South Jordan, UT (US)

(72) Inventors: John William Hall, North Salt Lake, UT (US); Craig Nordhausen, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 309 days.

(21) Appl. No.: 15/910,273

(22) Filed: Mar. 2, 2018

(65) Prior Publication Data
US 2018/0250025 A1  Sep. 6, 2018

Related U.S. Application Data

(60) Provisional application No. 62/467,554, filed on Mar. 6, 2017.

(51) Int. Cl.
*A61B 17/22* (2006.01)
*A61M 3/02* (2006.01)
(Continued)

(52) U.S. Cl.
CPC .............. *A61B 17/22* (2013.01); *A61B 17/32* (2013.01); *A61B 17/320758* (2013.01);
(Continued)

(58) Field of Classification Search
CPC . A61B 17/22; A61B 17/32; A61B 17/320758; A61B 2017/22062; A61B 2017/22079; A61B 2017/320004; A61B 2017/320775; A61B 2217/005; A61B 2017/320056; A61B 90/70; A61B 2090/701; A61M 1/3655; A61M 3/0279; A61M 25/0068; A61M 39/0247; A61M 39/10; A61M 25/0041; A61M 25/0074; A61M 25/0108; A61M 2025/0019;
(Continued)

(56) References Cited

U.S. PATENT DOCUMENTS 3,357,432 A   12/1967  Sparks
3,435,823 A    4/1969  Edwards
(Continued)

FOREIGN PATENT DOCUMENTS

DE   4418910    12/1995
DE   29515546   3/1997
(Continued)

OTHER PUBLICATIONS

Office Action dated Aug. 21, 2019 for U.S. Appl. No. 14/192,567.
(Continued)

*Primary Examiner* — Adam Marcetich
(74) *Attorney, Agent, or Firm* — Stoel Rives LLP

(57) ABSTRACT

Methods of declotting vascular access technologies, such as vascular access assemblies that facilitate hemodialysis, are provided. The methods can include disposing a catheter within a patient to access a vascular access assembly within the heart of the patient. The catheter can be coupled to the vascular access assembly such that a clot can be evacuated from within the vascular access assembly via the catheter.

20 Claims, 13 Drawing Sheets

(51) Int. Cl.
    A61M 39/10      (2006.01)
    A61B 17/32      (2006.01)
    A61M 39/02      (2006.01)
    A61M 1/36       (2006.01)
    A61B 17/3207    (2006.01)
    A61M 25/00      (2006.01)
    A61M 25/01      (2006.01)

(52) U.S. Cl.
    CPC ........ *A61M 1/3655* (2013.01); *A61M 3/0279* (2013.01); *A61M 25/0068* (2013.01); *A61M 39/0247* (2013.01); *A61M 39/10* (2013.01); *A61B 2017/22062* (2013.01); *A61B 2017/22079* (2013.01); *A61B 2017/320004* (2013.01); *A61B 2017/320775* (2013.01); *A61B 2217/005* (2013.01); *A61M 25/0041* (2013.01); *A61M 25/0074* (2013.01); *A61M 25/0108* (2013.01); *A61M 2025/0019* (2013.01); *A61M 2039/0258* (2013.01); *A61M 2039/0273* (2013.01); *A61M 2039/1077* (2013.01); *A61M 2205/0266* (2013.01)

(58) Field of Classification Search
    CPC .. A61M 2039/0258; A61M 2039/0273; A61M 2025/0197; A61M 25/0194; A61M 1/3659; A61M 1/3661; A61M 2005/1403; A61M 1/3653; A61M 2039/0018
    See application file for complete search history.

(56) References Cited

U.S. PATENT DOCUMENTS

| | | |
|---|---|---|
| 3,490,438 A | 1/1970 | Lavender et al. |
| 3,683,926 A | 8/1972 | Suzuki |
| 3,814,137 A | 6/1974 | Martinez |
| 3,818,511 A | 6/1974 | Goldberg et al. |
| 3,826,257 A | 7/1974 | Buselmeier |
| 3,853,126 A | 12/1974 | Schulte |
| 3,882,862 A | 5/1975 | Berend |
| 3,998,222 A | 12/1976 | Shihata |
| 4,076,023 A | 2/1978 | Martinez |
| 4,133,312 A | 1/1979 | Burd |
| 4,184,489 A | 1/1980 | Burd |
| 4,214,586 A | 7/1980 | Mericle |
| 4,318,401 A | 3/1982 | Zimmerman |
| 4,366,819 A | 1/1983 | Kaster |
| 4,427,219 A | 1/1984 | Madej |
| 4,441,215 A | 4/1984 | Kaster |
| 4,447,237 A | 5/1984 | Frisch et al. |
| 4,496,349 A | 1/1985 | Cosentino |
| 4,496,350 A | 1/1985 | Cosentino |
| 4,503,568 A | 3/1985 | Madras |
| 4,550,447 A | 11/1985 | Seiler, Jr. |
| 4,619,641 A | 10/1986 | Schanzer |
| 4,655,771 A | 4/1987 | Wallersten |
| 4,723,948 A | 2/1988 | Clark et al. |
| 4,734,094 A | 3/1988 | Jacob et al. |
| 4,753,236 A | 6/1988 | Healy |
| 4,771,777 A | 9/1988 | Horzewski et al. |
| 4,772,268 A | 9/1988 | Bates |
| 4,786,345 A | 11/1988 | Wood |
| 4,790,826 A | 12/1988 | Elftman |
| 4,822,341 A | 4/1989 | Colone |
| 4,848,343 A | 7/1989 | Wallsten et al. |
| 4,850,999 A | 7/1989 | Planck |
| 4,877,661 A | 10/1989 | House et al. |
| 4,898,591 A | 2/1990 | Jang et al. |
| 4,898,669 A | 2/1990 | Tesio |
| 4,917,087 A | 4/1990 | Walsh et al. |
| 4,919,127 A | 4/1990 | Pell |
| 4,929,236 A | 5/1990 | Sampson |
| 4,955,899 A | 9/1990 | Della Corna et al. |
| 5,026,513 A | 6/1991 | House et al. |
| 5,041,098 A | 8/1991 | Loiterman et al. |
| 5,042,161 A | 8/1991 | Hodge |
| 5,053,023 A | 10/1991 | Martin |
| 5,061,275 A | 10/1991 | Wallsten et al. |
| 5,061,276 A | 10/1991 | Tu et al. |
| 5,064,435 A | 11/1991 | Porter |
| 5,104,402 A | 4/1992 | Melbin |
| 5,171,227 A | 12/1992 | Twardowski et al. |
| 5,171,305 A | 12/1992 | Schickling et al. |
| 5,192,289 A | 3/1993 | Jessen |
| 5,192,310 A | 3/1993 | Herweck et al. |
| 5,197,976 A | 3/1993 | Herweck et al. |
| 5,282,860 A | 2/1994 | Matsuno et al. |
| 5,330,500 A | 7/1994 | Song |
| 5,336,616 A | 8/1994 | Livesey et al. |
| 5,399,168 A | 3/1995 | Wadsworth |
| 5,405,320 A | 4/1995 | Twardowski et al. |
| 5,405,339 A | 4/1995 | Kohnen et al. |
| 5,454,790 A | 10/1995 | Dubrul |
| 5,474,268 A | 12/1995 | Yu |
| 5,474,563 A | 12/1995 | Myler et al. |
| 5,476,451 A | 12/1995 | Ensminger et al. |
| 5,496,294 A | 3/1996 | Hergenrother et al. |
| 5,509,897 A | 4/1996 | Twardowski et al. |
| 5,549,663 A | 8/1996 | Cottone, Jr. |
| 5,558,641 A | 9/1996 | Glantz et al. |
| 5,562,617 A | 10/1996 | Finch, Jr. et al. |
| 5,562,618 A | 10/1996 | Cai et al. |
| 5,591,226 A | 1/1997 | Trerotola et al. |
| 5,607,463 A | 3/1997 | Schwartz et al. |
| 5,624,413 A | 4/1997 | Markel et al. |
| 5,637,088 A | 6/1997 | Wenner et al. |
| 5,637,102 A | 6/1997 | Tolkoff et al. |
| 5,645,532 A | 7/1997 | Horgan |
| 5,647,855 A | 7/1997 | Trooskin |
| 5,669,637 A | 9/1997 | Chitty et al. |
| 5,669,881 A | 9/1997 | Dunshee |
| 5,674,272 A | 10/1997 | Bush et al. |
| 5,676,346 A | 10/1997 | Leinsing |
| 5,743,894 A | 4/1998 | Swisher |
| 5,755,773 A | 5/1998 | Schuster |
| 5,755,775 A | 5/1998 | Trerotola et al. |
| 5,792,104 A | 8/1998 | Speckman et al. |
| 5,797,879 A | 8/1998 | Decampli |
| 5,800,512 A | 9/1998 | Lentz et al. |
| 5,800,514 A | 9/1998 | Nunez et al. |
| 5,800,522 A | 9/1998 | Campbell |
| 5,810,870 A | 9/1998 | Myers et al. |
| 5,830,224 A | 11/1998 | Cohn et al. |
| 5,840,240 A | 11/1998 | Stenoien et al. |
| 5,866,217 A | 2/1999 | Stenoien et al. |
| 5,904,967 A | 5/1999 | Ezaki et al. |
| 5,931,829 A | 8/1999 | Burbank et al. |
| 5,931,865 A | 8/1999 | Silverman et al. |
| 5,957,974 A | 9/1999 | Thompson et al. |
| 5,997,562 A | 12/1999 | Zadno-Azizi |
| 6,001,125 A | 12/1999 | Golds et al. |
| 6,019,788 A | 2/2000 | Butters et al. |
| 6,036,724 A | 3/2000 | Lentz et al. |
| 6,102,884 A | 8/2000 | Squitieri |
| 6,156,016 A | 12/2000 | Maginot |
| 6,167,765 B1 | 1/2001 | Weitzel |
| 6,171,295 B1 | 1/2001 | Garabedian |
| 6,231,085 B1 | 5/2001 | Olson |
| 6,245,098 B1 | 6/2001 | Feeser |
| 6,255,396 B1 | 7/2001 | Ding et al. |
| 6,261,255 B1 | 7/2001 | Mullis et al. |
| 6,261,257 B1 | 7/2001 | Uflacker et al. |
| 6,280,466 B1 | 8/2001 | Kugler et al. |
| 6,308,992 B1 | 10/2001 | Mitsui et al. |
| 6,309,411 B1 | 10/2001 | Lashinski et al. |
| 6,319,279 B1 | 11/2001 | Shannon et al. |
| 6,338,724 B1 | 1/2002 | Dossa |
| 6,398,764 B1 | 6/2002 | Finch, Jr. et al. |
| 6,402,767 B1 | 6/2002 | Nash et al. |
| 6,428,571 B1 | 8/2002 | Lentz et al. |
| 6,436,132 B1 | 8/2002 | Patel et al. |
| 6,582,409 B1 | 6/2003 | Squitieri |
| 6,585,762 B1 | 7/2003 | Stanish |

(56) References Cited

U.S. PATENT DOCUMENTS

| | | |
|---|---|---|
| 6,610,004 B2 | 8/2003 | Viole et al. |
| 6,689,096 B1 | 2/2004 | Loubens et al. |
| 6,689,157 B2 | 2/2004 | Madrid et al. |
| 6,692,461 B2 | 2/2004 | Wantink |
| 6,699,233 B2 | 3/2004 | Slanda et al. |
| 6,702,748 B1 | 3/2004 | Nita et al. |
| 6,702,781 B1 | 3/2004 | Reifart et al. |
| 6,706,025 B2 | 3/2004 | Engelson et al. |
| 6,719,781 B1 | 4/2004 | Kim |
| 6,719,783 B2 | 4/2004 | Lentz et al. |
| 6,730,096 B2 | 5/2004 | Basta |
| 6,733,459 B1 | 5/2004 | Atsumi |
| 6,740,273 B2 | 5/2004 | Lee |
| 6,749,574 B2 | 6/2004 | O'Keefe |
| 6,752,826 B2 | 6/2004 | Holloway et al. |
| 6,758,836 B2 | 7/2004 | Zawacki |
| 6,858,019 B2 | 2/2005 | McGuckin, Jr. et al. |
| 6,926,724 B1 | 8/2005 | Chu |
| 6,926,735 B2 | 8/2005 | Henderson |
| 6,976,952 B1 | 12/2005 | Maini et al. |
| 6,981,987 B2 | 1/2006 | Huxel et al. |
| 7,011,645 B2 | 3/2006 | McGuckin, Jr. et al. |
| 7,025,741 B2 | 4/2006 | Cull |
| 7,044,937 B1 | 5/2006 | Kirwan et al. |
| 7,101,356 B2 | 9/2006 | Miller |
| 7,131,959 B2 | 11/2006 | Blatter |
| 7,211,074 B2 | 5/2007 | Sansoucy |
| 7,244,271 B2 | 7/2007 | Lenz et al. |
| 7,244,272 B2 | 7/2007 | Dubson et al. |
| 7,252,649 B2 | 8/2007 | Sherry |
| 7,297,158 B2 | 11/2007 | Jensen |
| 7,351,257 B2 * | 4/2008 | Kaldany .................. A61F 2/07 623/1.27 |
| 7,399,296 B2 | 7/2008 | Poole et al. |
| 7,438,699 B2 | 10/2008 | Pecor et al. |
| 7,452,374 B2 | 11/2008 | Hain et al. |
| 7,507,229 B2 | 3/2009 | Hewitt et al. |
| 7,588,551 B2 | 9/2009 | Gertner |
| 7,708,722 B2 | 5/2010 | Glenn |
| 7,722,665 B2 | 5/2010 | Anwar et al. |
| RE41,448 E | 7/2010 | Squitieri |
| 7,762,977 B2 | 7/2010 | Porter et al. |
| 7,789,908 B2 | 9/2010 | Sowinski et al. |
| 7,828,833 B2 | 11/2010 | Haverkost et al. |
| 7,833,214 B2 | 11/2010 | Wilson et al. |
| 7,846,139 B2 | 12/2010 | Zinn et al. |
| 7,850,675 B2 | 12/2010 | Bell et al. |
| 7,850,705 B2 | 12/2010 | Bachinski et al. |
| 7,922,757 B2 | 4/2011 | McGuckin |
| 7,972,314 B2 | 7/2011 | Bizup et al. |
| 8,079,973 B2 | 12/2011 | Herrig et al. |
| 8,092,435 B2 | 1/2012 | Beling et al. |
| 8,313,524 B2 | 11/2012 | Edwin et al. |
| 8,388,634 B2 | 3/2013 | Rubenstein et al. |
| 8,512,312 B2 | 8/2013 | Sage |
| 8,551,139 B2 * | 10/2013 | Surti .................. A61B 17/0401 606/232 |
| 8,690,815 B2 | 4/2014 | Porter et al. |
| 8,951,355 B2 * | 2/2015 | Boyle, Jr. .............. A61B 90/70 134/8 |
| 9,642,623 B2 | 5/2017 | Agarwal et al. |
| 9,731,113 B2 * | 8/2017 | Grace .................. A61N 1/05 |
| 10,172,673 B2 * | 1/2019 | Viswanathan ......... A61N 1/056 |
| 2001/0053930 A1 | 12/2001 | Kugler et al. |
| 2002/0049403 A1 | 4/2002 | Alanis |
| 2002/0055766 A1 | 5/2002 | Wallace et al. |
| 2002/0055771 A1 | 5/2002 | Sandock |
| 2002/0069893 A1 * | 6/2002 | Kawazoe ................ A61B 1/122 134/1 |
| 2002/0099432 A1 | 7/2002 | Yee |
| 2002/0151761 A1 | 10/2002 | Viole et al. |
| 2003/0100859 A1 | 5/2003 | Henderson et al. |
| 2003/0135258 A1 | 7/2003 | Andreas et al. |
| 2003/0135261 A1 | 7/2003 | Kugler et al. |
| 2003/0139806 A1 | 7/2003 | Haverkost et al. |
| 2003/0181969 A1 | 9/2003 | Kugler et al. |
| 2003/0212385 A1 | 11/2003 | Brenner et al. |
| 2003/0212431 A1 | 11/2003 | Brady et al. |
| 2004/0024442 A1 | 2/2004 | Sowinkski et al. |
| 2004/0054405 A1 | 3/2004 | Thierry et al. |
| 2004/0073282 A1 | 4/2004 | Stanish |
| 2004/0078071 A1 | 4/2004 | Escamilla et al. |
| 2004/0092956 A1 * | 5/2004 | Liddicoat ............ A61M 27/008 606/127 |
| 2004/0147866 A1 | 7/2004 | Blatter et al. |
| 2004/0193242 A1 | 9/2004 | Lentz et al. |
| 2004/0215058 A1 | 10/2004 | Zirps et al. |
| 2004/0215337 A1 | 10/2004 | Hain et al. |
| 2004/0236412 A1 * | 11/2004 | Brar .................... A61F 2/88 623/1.31 |
| 2005/0004553 A1 | 1/2005 | Douk |
| 2005/0137614 A1 | 6/2005 | Porter et al. |
| 2005/0192559 A1 | 9/2005 | Michels et al. |
| 2005/0203457 A1 | 9/2005 | Smego |
| 2005/0209581 A1 | 9/2005 | Butts et al. |
| 2005/0215938 A1 | 9/2005 | Khan et al. |
| 2006/0004392 A1 | 1/2006 | Amarant |
| 2006/0029465 A1 | 2/2006 | Auer |
| 2006/0058867 A1 | 3/2006 | Thistle et al. |
| 2006/0064159 A1 | 3/2006 | Porter et al. |
| 2006/0081260 A1 | 4/2006 | Eells et al. |
| 2006/0118236 A1 | 6/2006 | House et al. |
| 2007/0038288 A1 | 2/2007 | Lye et al. |
| 2007/0078412 A1 | 4/2007 | McGuckin, Jr. et al. |
| 2007/0078416 A1 | 4/2007 | Eliasen |
| 2007/0078438 A1 | 4/2007 | Okada |
| 2007/0088336 A1 | 4/2007 | Dalton |
| 2007/0123811 A1 | 5/2007 | Squitieri |
| 2007/0135775 A1 | 6/2007 | Edoga et al. |
| 2007/0142850 A1 | 6/2007 | Fowler |
| 2007/0161958 A1 | 7/2007 | Glenn |
| 2007/0167901 A1 | 7/2007 | Herrig et al. |
| 2007/0168019 A1 | 7/2007 | Amplatz et al. |
| 2007/0173868 A1 | 7/2007 | Bachinski et al. |
| 2007/0179513 A1 * | 8/2007 | Deutsch .............. A61B 17/221 606/159 |
| 2007/0191779 A1 | 8/2007 | Shubayev et al. |
| 2007/0197856 A1 | 8/2007 | Gellman et al. |
| 2007/0213838 A1 | 9/2007 | Hengelmolen |
| 2007/0219510 A1 | 9/2007 | Zinn et al. |
| 2007/0233018 A1 | 10/2007 | Bizup et al. |
| 2007/0249986 A1 | 10/2007 | Smego |
| 2007/0249987 A1 | 10/2007 | Gertner |
| 2007/0265584 A1 | 11/2007 | Hickman et al. |
| 2007/0293823 A1 | 12/2007 | Sherry |
| 2007/0293829 A1 | 12/2007 | Conlon et al. |
| 2008/0009781 A1 | 1/2008 | Anwar et al. |
| 2008/0027534 A1 | 1/2008 | Edwin et al. |
| 2008/0132924 A1 | 6/2008 | McGuckin |
| 2008/0167595 A1 | 7/2008 | Porter et al. |
| 2008/0221469 A1 | 9/2008 | Shevchuk |
| 2008/0267688 A1 * | 10/2008 | Busted .................. A61B 1/122 401/190 |
| 2008/0306580 A1 | 12/2008 | Jenson et al. |
| 2009/0076587 A1 | 3/2009 | Cully et al. |
| 2009/0137944 A1 | 5/2009 | Haarala et al. |
| 2009/0179422 A1 | 7/2009 | Werth |
| 2009/0227932 A1 | 9/2009 | Herrig |
| 2009/0234267 A1 | 9/2009 | Ross |
| 2009/0318895 A1 | 12/2009 | Lachner |
| 2010/0154800 A1 | 6/2010 | Chang et al. |
| 2010/0160847 A1 | 6/2010 | Braido et al. |
| 2010/0161040 A1 | 6/2010 | Braido et al. |
| 2010/0198079 A1 | 8/2010 | Ross |
| 2010/0268188 A1 | 10/2010 | Hanson |
| 2010/0268196 A1 | 10/2010 | Hastings et al. |
| 2010/0292774 A1 | 11/2010 | Shalev |
| 2011/0015723 A1 | 1/2011 | Batiste et al. |
| 2011/0054312 A1 | 3/2011 | Bell et al. |
| 2011/0060264 A1 | 3/2011 | Porter et al. |
| 2011/0106019 A1 * | 5/2011 | Bagwell .............. B08B 9/0436 604/267 |
| 2011/0112482 A1 | 5/2011 | Redd |
| 2011/0196282 A1 | 8/2011 | Kassab |

(56) References Cited

U.S. PATENT DOCUMENTS

| | | |
|---|---|---|
| 2011/0208218 A1 | 8/2011 | Ball |
| 2011/0257609 A1 | 10/2011 | Bizup et al. |
| 2011/0264080 A1 | 10/2011 | Lim et al. |
| 2011/0295181 A1 | 12/2011 | Dann et al. |
| 2012/0059305 A1 | 3/2012 | Akingba |
| 2012/0065652 A1 | 3/2012 | Cully et al. |
| 2012/0078202 A1 | 3/2012 | Beling et al. |
| 2013/0060268 A1 | 3/2013 | Herrig |
| 2013/0338559 A1 | 12/2013 | Franano et al. |
| 2014/0018721 A1 | 1/2014 | Gage et al. |
| 2014/0094841 A1 | 4/2014 | Sutton et al. |
| 2014/0150782 A1* | 6/2014 | Vazales .............. A61M 16/0463 128/202.16 |
| 2014/0155908 A1* | 6/2014 | Rosenbluth ...... A61B 17/32075 606/127 |
| 2014/0257244 A1* | 9/2014 | Johnston ............ A61M 25/0017 604/508 |
| 2014/0276215 A1 | 9/2014 | Nelson |
| 2014/0288638 A1 | 9/2014 | Knight et al. |
| 2014/0296822 A1* | 10/2014 | Chartrand .............. A61B 90/70 604/500 |
| 2014/0371779 A1* | 12/2014 | Vale ................ A61B 17/320725 606/200 |
| 2015/0051532 A1 | 2/2015 | Tomko et al. |
| 2015/0082604 A1 | 3/2015 | Cully et al. |
| 2015/0094744 A1 | 4/2015 | Aghayev et al. |
| 2015/0150640 A1 | 6/2015 | Boyle et al. |
| 2015/0165496 A1* | 6/2015 | Moreau ................. A61M 39/20 134/22.12 |
| 2015/0257775 A1* | 9/2015 | Gilvarry .............. A61B 17/221 606/127 |
| 2016/0066954 A1 | 3/2016 | Miller et al. |
| 2016/0120673 A1* | 5/2016 | Siegel ....................... A61F 2/95 623/1.23 |
| 2016/0129177 A1 | 5/2016 | Herrig |
| 2016/0136398 A1* | 5/2016 | Heilman ........... A61M 25/0155 604/9 |
| 2017/0020556 A1 | 1/2017 | Sutton et al. |
| 2017/0106128 A1* | 4/2017 | Bagwell .............. A61M 1/0084 |
| 2019/0015627 A1 | 1/2019 | Hall et al. |
| 2019/0022368 A1 | 1/2019 | Hall et al. |

FOREIGN PATENT DOCUMENTS

| | | |
|---|---|---|
| DE | 102008055587 | 8/2009 |
| EP | 1797831 | 6/2007 |
| JP | 62112567 | 5/1987 |
| JP | 04507050 | 12/1992 |
| JP | 05212107 | 8/1993 |
| JP | 06105798 | 4/1994 |
| JP | 09084871 | 3/1997 |
| JP | 09264468 | 7/1997 |
| JP | 2003501223 | 1/2003 |
| JP | 3995057 | 10/2007 |
| JP | 2008511414 | 4/2008 |
| KR | 101026933 | 4/2011 |
| KR | 1020110036848 | 4/2011 |
| WO | 198403036 | 8/1984 |
| WO | 199008509 | 8/1990 |
| WO | 199519200 | 7/1995 |
| WO | 199624399 | 8/1996 |
| WO | 1998034676 | 8/1998 |
| WO | 2000027299 | 5/2000 |
| WO | 200076577 | 12/2000 |
| WO | 200105447 | 1/2001 |
| WO | 200105463 | 1/2001 |
| WO | 2001005463 | 1/2001 |
| WO | 2001028456 | 4/2001 |
| WO | 200238198 | 5/2002 |
| WO | 2004032991 | 4/2004 |
| WO | 2004112880 | 12/2004 |
| WO | 2006026687 | 9/2006 |
| WO | 2009059371 | 5/2009 |
| WO | 2009082513 | 7/2009 |
| WO | 2009120400 | 10/2009 |
| WO | 2010059102 | 5/2010 |
| WO | 2011060386 | 5/2011 |
| WO | 2011153302 | 12/2011 |
| WO | 2015100251 | 7/2015 |

OTHER PUBLICATIONS

Peterson, et al., Subclavian Venous Stenosis: A Complication of Subclavian Dialysis, The Journal of American Medical Association, vol. 252 No. 24 ,Dec. 28, 1994 ,3404-3406.
Raju M.D., et al., Techniques for Insertion and Management of Complications, PTFE Grafts for Hemodialysis Access, Ann. Surg., vol. 206 No. 5 ,Nov. 1987 ,666-673.
Sharafuddin, et al., Percutaneous Balloon-Assisted Aspiration Thrombectomy of clotted ahemodialysis Access Grafts, Journal of Vascular and Interventional Radiology, vol. 7 No. 2 ,Mar.-Apr. 1996 ,177-183.
Office Action dated Sep. 26, 2019 for U.S. Appl. No. 15/693,010.
International Search Report and Written Opinion dated Jun. 15, 2018 for PCT/US2018/020614.
European Search Report dated Jun. 8, 2005 for EP05006233.0.
European Search Report dated Dec. 3, 2013 for EP05793066.1.
International Preliminary Report dated Mar. 12, 2014 for PCT/US2012/053967.
International Search Report and Written Opinion dated Jan. 18, 2019 for PCT/US2018/041821.
International Search Report and Written Opinion dated Jan. 28, 2015 for PCT/US2014/049547.
International Search Report and Written Opinion dated Mar. 15, 2013 for PCT/US2012/053967.
International Search Report and Written Opinion dated Mar. 16, 2015 for PCT/US2014/046630.
International Search Report and Written Opinion dated May 2, 2018 for PCT/US2018/013326.
International Search Report and Written Opinion dated May 3, 2013 for PCT/US2012/053967.
International Search Report and Written Opinion dated May 6, 1998 for PCT/US1998/001939.
International Search Report and Written Opinion dated Jun. 3, 2009 for PCT/US2009/035923.
International Search Report and Written Opinion dated Jun. 20, 2007 for PCT/US2006/044564.
International Search Report and Written Opinion dated Jul. 17, 2018 for PCT/US2018/023956.
International Search Report and Written Opinion dated Oct. 30, 2018 for PCT/US2018/042900.
International Search Report and Written Opinion dated Jun. 22, 2018 for PCT/US2018/014371.
Notice of Allowance dated Mar. 15, 2010 for U.S. Appl. No. 11/216,536.
Notice of Allowance dated Oct. 4, 2013 for U.S. Appl. No. 12/831,092.
Notice of Allowance dated Oct. 5, 2018 for U.S. Appl. No. 15/093,622.
Notice of Allowance dated Nov. 6, 2018 for U.S. Appl. No. 14/995,270.
Office Action dated Jan. 8, 2019 for U.S. Appl. No. 15/035,626.
Office Action dated Jan. 9, 2018 for U.S. Appl. No. 14/450,468.
Office Action dated Feb. 6, 2013 for U.S. Appl. No. 12/831,092.
Office Action dated Feb. 21, 2017 for U.S. Appl. No. 14/192,567.
Office Action dated Mar. 15, 2018 for U.S. Appl. No. 14/332,091.
Office Action dated May 5, 2010 for U.S. Appl. No. 10/962,200.
Office Action dated May 24, 2018 for U.S. Appl. No. 14/995,270.
Office Action dated Jun. 4, 2018 for U.S. Appl. No. 14/192,567.
Office Action dated Jun. 9, 2016 for U.S. Appl. No. 14/192,567.
Office Action dated Jun. 15, 2017 for U.S. Appl. No. 14/192,567.
Office Action dated Jul. 11, 2018 for U.S. Appl. No. 14/450,468.
Office Action dated Jul. 19, 2018 for U.S. Appl. No. 15/035,626.
Office Action dated Aug. 7, 2017 for U.S. Appl. No. 14/450,468.
Office Action dated Aug. 12, 2010 for U.S. Appl. No. 10/962,200.
Office Action dated Aug. 15, 2016 for U.S. Appl. No. 14/332,091.

(56) References Cited

OTHER PUBLICATIONS

Office Action dated Sep. 20, 2012 for U.S. Appl. No. 12/831,092.
Office Action dated Oct. 1, 2018 for U.S. Appl. No. 14/332,091.
Office Action dated Oct. 27, 2015 for U.S. Appl. No. 14/192,567.
Office Action dated Nov. 26, 2007 for U.S. Appl. No. 10/962,200.
Office Action dated Dec. 5, 2017 for U.S. Appl. No. 14/995,270.
Office Action dated Dec. 5, 2018 for U.S. Appl. No. 14/450,468.
Office Action dated Dec. 7, 2018 for U.S. Appl. No. 14/192,567.
Office Action dated Dec. 20, 2017 for U.S. Appl. No. 14/192,567.
Office Action dated Dec. 30, 2016 for U.S. Appl. No. 14/450,468.
Clinical Reveiw of MTI, Onxy Liquid Embolization System, available at http://www.fda.gov/ohrms/dockets/ac/03/briefing/3975b1-02-clinical-review.pdf. accessed Aug. 29, 2005.
Besarab, et al., Measuring the Adequacy of Hemodialysis Access, Current Opinion in Nephrology and Hypertension, Rapid Science Publishers ISSN ,1996 ,1062-4821.
Coulson MD, et al., Modification of Venous End of Dialysis Grafts: An Attempt to Reduce Neointimal Hyperplasia, Dialysis & Transplantation, vol. 29 No. 1 ,Jan. 2000 ,10-18.
Coulson MD, PhD, et al., A Combination of the Elephant Trunk Anastomosis Technique and Vascular Clips for Dialysis Grafts, Surgical Rounds ,Nov. 1999 ,596-608.
Kanterman, et al., Dialysis Access Grafts: Anatomic Location of Venous Stenosis and Results of Angioplasty, Interventional Radiology, vol. 195 No. 1, 195 ,Apr. 1995 ,135-139.
Kumpe, et al., Angioplasty/Thrombolytic Treatment of Failing and Failed Hemodialysis Access Sites: Comparison with Surgical Treatment, Progress in Cardiovascular Diseases, vol. XXXIV No. 4 ,Jan./Feb. 1992 ,263-278.
Lin, et al., Contemporary Vascular Access Surgery for Chronic Haemodialysis, They Royal College of Surgeons of Edinburgh, J.R. Coll, Surg, Edinb., 41 ,Jun. 1996 ,164-169.
Office Action dated May 1, 2020 for U.S. Appl. No. 15/693,010.
Office Action dated Oct. 1, 2020 for U.S. Appl. No. 15/868,313.
Office Action dated Apr. 16, 2020 for U.S. Appl. No. 15/868,313.
Office Action dated Apr. 28, 2020 for U.S. Appl. No. 14/192,567.
European Search Report dated Oct. 26, 2020 for EP18738538.0.
European Search Report dated Dec. 4, 2020 for 18764826.6.
Office Action dated Dec. 7, 2020 for U.S. Appl. No. 16/033,515.
Office Action dated Mar. 29, 2021 for U.S. Appl. No. 16/033,515.

\* cited by examiner

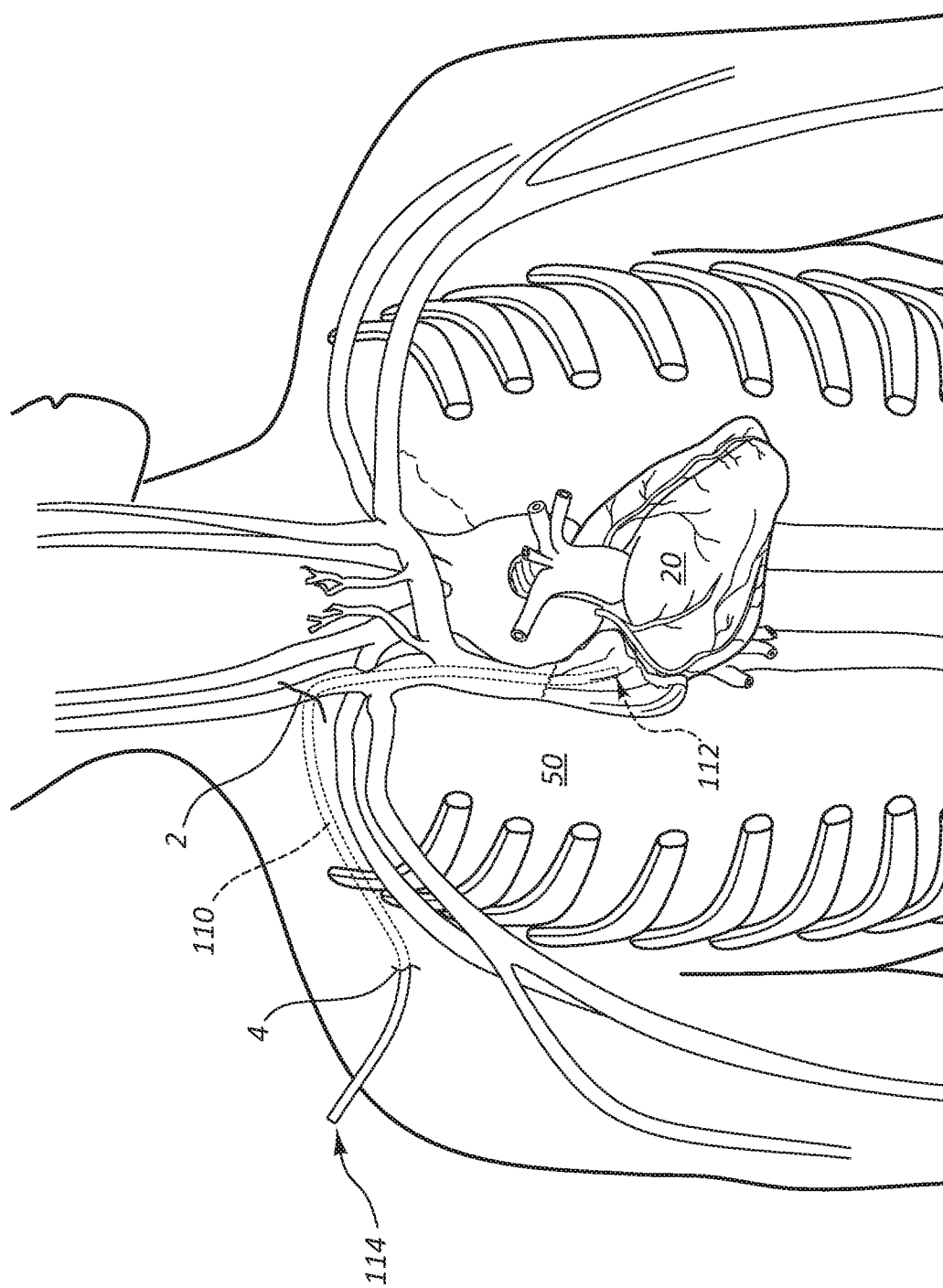

VASCULAR ACCESS ASSEMBLY DECLOTTING SYSTEMS AND METHODS

RELATED APPLICATIONS

This application claims priority to U.S. Provisional Application No. 62/467,554, filed on Mar. 6, 2017 and titled, "Vascular Access Assembly Declotting Systems and Methods," which is hereby incorporated by reference in its entirety.

TECHNICAL FIELD

The present disclosure relates generally to systems for declotting vascular access technologies, such as vascular access assemblies that facilitate hemodialysis. The present disclosure also relates generally to methods of declotting vascular access assemblies. In some embodiments, the present disclosure relates to methods of accessing vascular access assemblies within the vena cava or right atrium of the heart. The disclosure also relates to methods of coupling a catheter of the system to a vascular access assembly such that a clot can be evacuated from within the vascular access assembly.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 2B depicts the first tubular conduit placed into the patient such that a peripheral end of the first tubular conduit is disposed adjacent an incision in the shoulder region of the patient.

FIG. 3C-1 is a detail view of the central end portions of the catheter and the first tubular conduit in a decoupled configuration.

FIG. 3C-2 is a detail view of the central end portions of the catheter and the first tubular conduit in a coupled configuration.

FIG. 3C-3 is a detail view of a central end portion of another embodiment of a first tubular conduit.

FIG. 4C-1 is a detail view of the central end portions of the catheter and the first tubular conduit in a decoupled configuration.

FIG. 4C-2 is a detail view of the central end portions of the catheter and the first tubular conduit in a coupled configuration.

DETAILED DESCRIPTION

Figure 1:
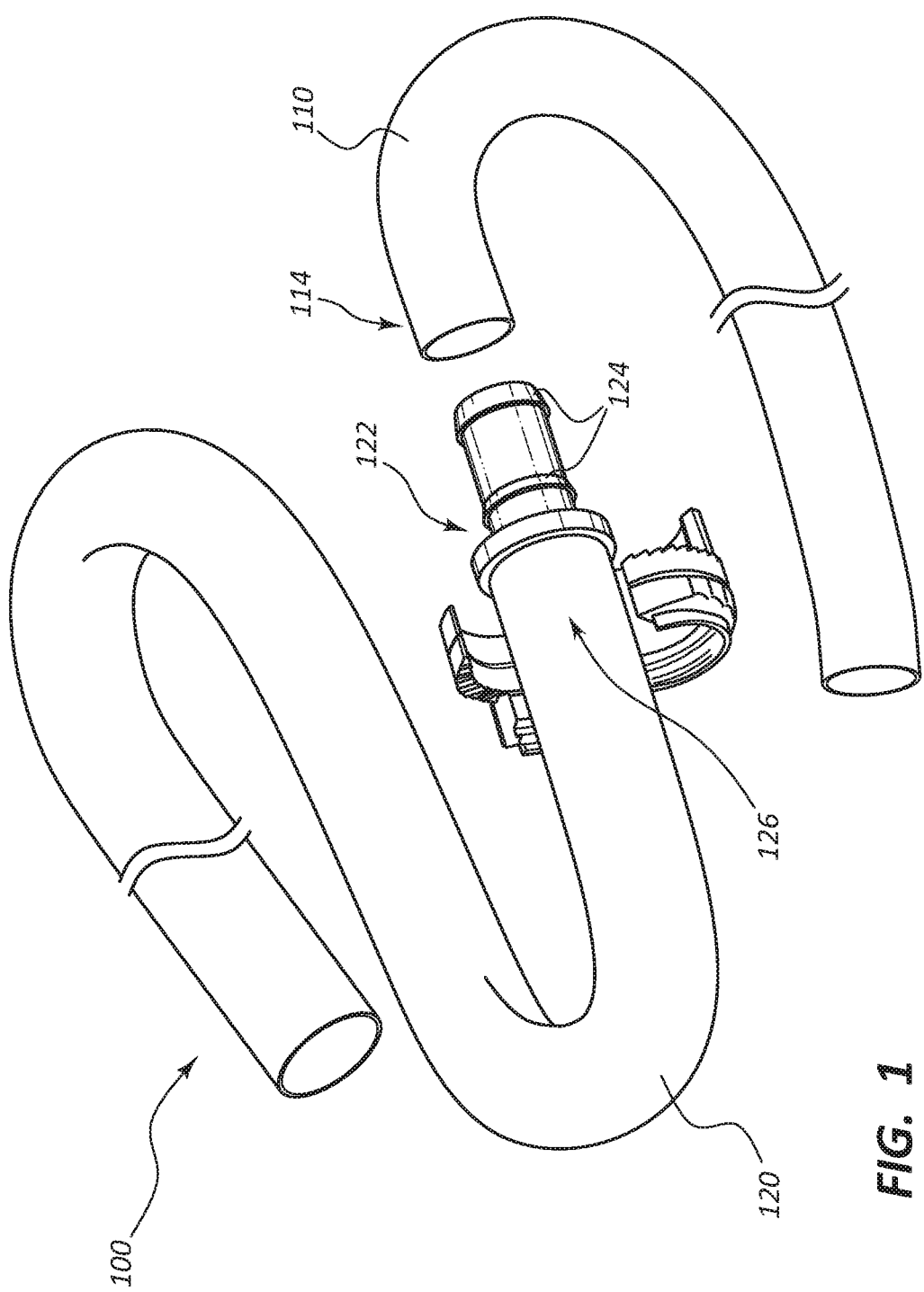
FIG. 1 is a perspective view of a vascular access assembly.

Many patients who suffer from kidney malfunction undergo hemodialysis to remove waste products from their blood. Hemodialysis generally requires access to an adequate blood supply. In some cases, access to a blood supply may be established via an arteriovenous fistula. In other circumstances, other methods for accessing the blood supply are used.

For example, in some embodiments, access to a blood supply is established via an arteriovenous graft. In other embodiments, access to a blood supply is established via a graft that extends from a peripheral blood supply to an outlet that is positioned in the central venous system.

Certain embodiments disclosed herein may be used to establish an artificial blood flow path, such as along a non-natural or artificial conduit, that improves or provides alternative access to a blood supply. The artificial flow path may be used, for example, to bypass a central venous stenosis. In some embodiments, the artificial blood flow path, when implanted into a patient, is fully subcutaneous. Access to a blood supply that is provided by an artificial flow path may be particularly advantageous for access in hemodialysis patients (such as hemodialysis patients who have exhausted peripheral venous access sites for fistulas).

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Thus, two components may be coupled to each other even though they are not in direct contact with each other. For example, two components may be coupled to each other through an intermediate component. The phrase "attached to" refers to interaction between two or more entities which are in direct contact with each other and/or are separated from each other only by a fastener of any suitable variety (e.g., an adhesive). The phrase "fluid communication" is broad enough to refer to arrangements in which a fluid (e.g., blood) can flow from one element to another element when the elements are in fluid communication with each other. Unless otherwise stated, all ranges include both endpoints and all numbers between the endpoints.

The terms "central" and "peripheral," as used herein, are opposite directional terms along a flow path of the vasculature. For example, a peripheral end of a device or component is the end of the device or component that is furthest from the heart when the device or component is assembled and implanted within the patient. The central end portion refers to the opposite end or the end closest to the heart of the patient when the device is in use. Further, this reference frame is applied herein to devices configured or designed to have one end (a central end) positioned closer to the heart when the device is in use, whether or not the device itself is deployed within the body.

FIG. 1 provides a perspective view of a vascular access assembly 100. As shown, the vascular access assembly 100 can include a first tubular conduit 110, a second tubular conduit 120, and one or more connectors or adaptors 122. In some embodiments, the first tubular conduit 110 may have an initial length of at least 20 cm, at least 25 cm, at least 30 cm, or at least 35 cm. For example, the first tubular conduit 110 may have an initial length of between about 20 cm and about 50 cm or between about 35 cm and about 45 cm. In certain embodiments, the first tubular conduit 110 has an internal diameter of between about 3.5 mm and about 6.5 mm. For example, the internal diameter of the first tubular conduit 110 may be between about 4.5 mm and about 5.5 mm.

In various embodiments, the first tubular conduit 110 may be resistant to kinking and/or crush forces. The first tubular conduit 110 may be reinforced. For example, the first tubular conduit 110 may be reinforced with nitinol, such as braided nitinol, which can provide resistance to kinking and/or crush forces. More specifically, in various embodiments, the first tubular conduit 110 may include silicone-coated nitinol.

In some embodiments, the first tubular conduit 110 may include one or more radiopaque bands or markers (not shown). For example, the first tubular conduit 110 may include a radiopaque band adjacent the central end portion of the first tubular conduit 110. The radiopaque band(s) or marker(s) may facilitate fluoroscopic placement of the first tubular conduit 110 within a patient.

In certain embodiments, the second tubular conduit 120 may be configured to be accessed for hemodialysis. In other words, during some medical procedures (e.g., hemodialysis), the second tubular conduit 120 may be accessed in lieu of the natural vasculature of a patient. In various embodiments, the second tubular conduit 120 may include and/or consist of polytetrafluoroethylene (PTFE) (e.g., such as expanded PTFE (ePTFE), rotational spun PTFE, or electrospun PTFE). In various other embodiments, the second tubular conduit 120 may include silicone, a fibrous polymer, or another suitable material.

In some embodiments, the second tubular conduit 120 may include a puncturable and self-sealing wall such that the wall may be punctured by insertion of a needle and then reseal upon withdrawal of the needle. The self-sealing wall may be of any suitable composition. In certain embodiments, the self-sealing wall may be a multi-layered construct. For example, the self-sealing wall may include an outer layer, an inner layer, and at least one tie layer disposed between the outer layer and the inner layer. One or more of the outer layer and the inner layer may include PTFE. For example, the outer layer may include and/or consist of expanded PTFE while the inner layer may include and/or consist of rotational spun or electrospun PTFE. The tie layer may include an elastomer such as elastomeric silicone. Due, at least in part, to the properties of the silicone, the resulting construct may be self-sealing. In other words, when a needle that has been inserted through the wall is withdrawn from the second tubular conduit 120, the wall may seal itself, thereby preventing leakage of blood from the second tubular conduit 120.

In various embodiments, the second tubular conduit 120 may have an initial length of at least 30 cm, at least 40 cm, or at least 45 cm. For example, the second tubular conduit 120 may be between about 30 cm and about 70 cm or between about 40 cm and about 60 cm in length. In some embodiments, the second tubular conduit 120 may have an internal diameter of between about 4.5 mm and about 8 mm. For example, the internal diameter of the second tubular conduit 120 may be between about 5.5 mm and about 6.5 mm.

In some embodiments, both the first tubular conduit 110 and the second tubular conduit 120 may be self-sealing. In some other embodiments, only the second tubular conduit 120 may be self-sealing.

In certain embodiments, one or both of an inner surface and an outer surface of the vascular access assembly 100 may be associated with a therapeutic agent. In other words, the therapeutic agent may be disposed on or embedded within a surface of the vascular access assembly 100. The therapeutic agent may be released from the surface(s) of the vascular access assembly 100 to deliver a therapeutically effective dose of the therapeutic agent to the patient when the vascular access assembly 100 is implanted within a patient. In various embodiments, a first therapeutic agent is associated with the inner surface of the vascular access assembly 100 and a second therapeutic agent that differs from the first therapeutic agent is associated with the outer surface of the vascular access assembly 100. In such embodiments, both the first therapeutic agent and the second therapeutic agent may be delivered into the bloodstream of the patient in therapeutically effective doses when the vascular access assembly 100 is implanted within the patient. In some embodiments, heparin may be used as a therapeutic agent. The therapeutic agent may reduce or be configured to reduce thrombus or tissue proliferation.

With continued reference to FIG. 1, the one or more connectors 122 may facilitate coupling of the first tubular conduit 110 to the second tubular conduit 120, or vice versa. In certain embodiments, such as the embodiment shown in FIG. 1, the connector 122 can be disposed at a central end 126 the second tubular conduit 120.

As depicted, the connector 122 may include one or more barbs or protrusions 124 that are designed to engage with an inner surface of the first tubular conduit 110 to form a fluid-tight connection. While FIG. 1 shows the connector 122 at the central end 126 of the second tubular conduit 120, a skilled artisan will recognize that, in other embodiments, the connector 122 may instead be disposed at a peripheral end 114 of the first tubular conduit 110. In still other embodiments, the connector 122 may include components disposed at both the central end 126 of the second tubular conduit 120 and the peripheral end 114 of the first tubular conduit 110. The connector 122 may be made from any suitable material, such as a metal (e.g., steel or titanium), a polymer, etc.

The vascular access assembly 100 may be used in any suitable medical procedure, such as to establish vascular access for hemodialysis. For example, where a vein has become stenotic or otherwise failed an artificial flow path that bypasses the stenosis or failure may be established. Stated another way, an artificial flow path may be established from a target site (e.g., from a target site in a vessel, artery, arteriovenous graft, etc.) to the vena cava or right atrium of the heart. Various examples herein discuss access and therapies performed in the right atrium of the heart. These examples and related disclosure may be analogously applied to access and therapies performed at adjacent locations such as the vena cava or the venous vasculature around the vena cava. Still further, while specific examples and disclosure below may refer to systems disposed within veins of a patient, any of the methods for declotting conduits, closing or sealing conduits, and so forth may be analogously applied to a variety of vessels, including veins, arteries, ducts, vessels, and other locations within the body.

Figure 2A:
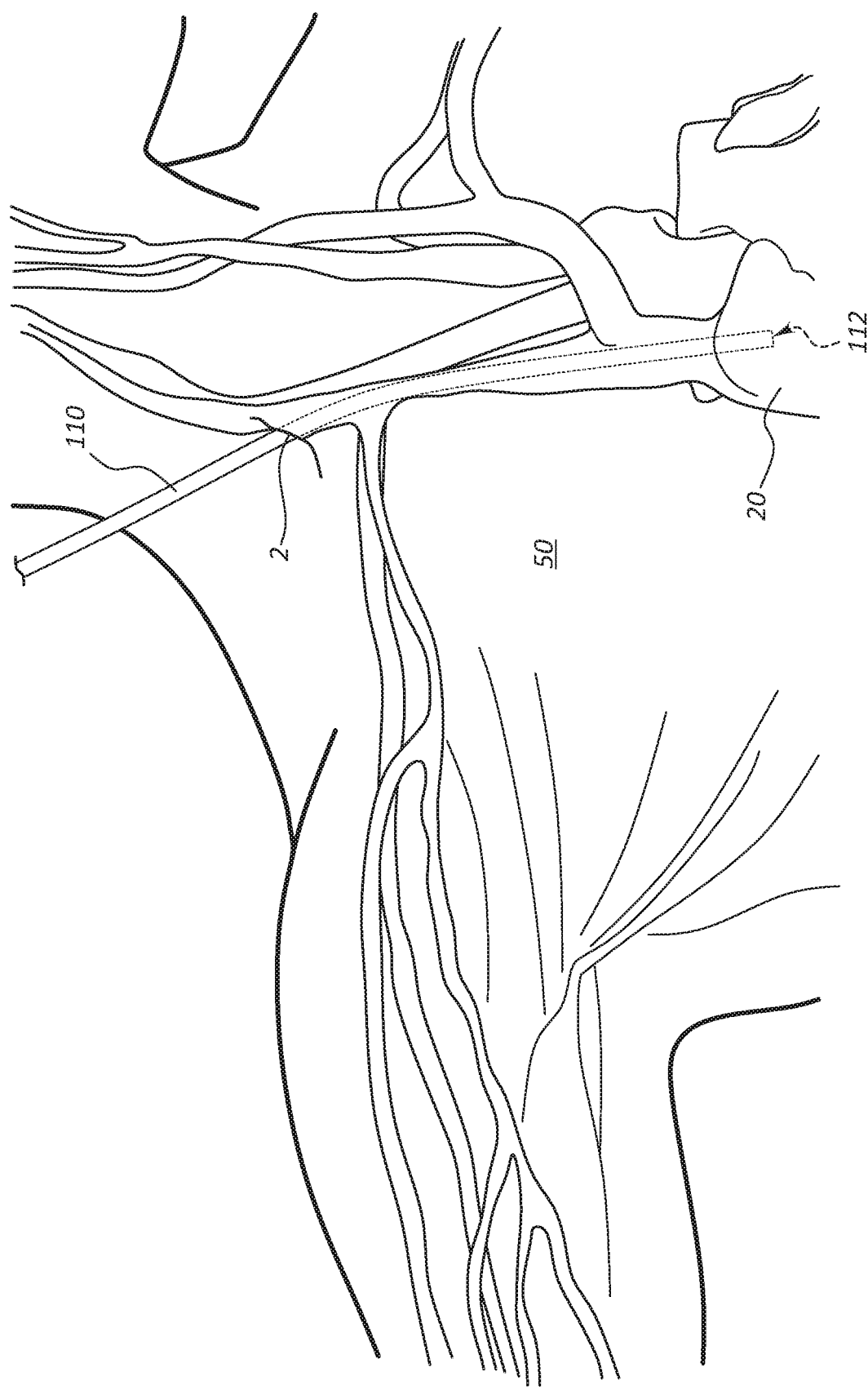
FIG. 2A depicts a first tubular conduit of the vascular access assembly of FIG. 1 that has been inserted into a patient such that a central end portion of the first tubular conduit is disposed within the right atrium of the patient.

As shown in FIG. 2A, such a medical procedure may initially involve making a first incision 2 at or adjacent to the neck of a patient 50 to access the right internal jugular vein of the patient 50. A guidewire may then be passed into the right internal jugular vein to the inferior vena cava, followed by a dilator that is passed over the guidewire to facilitate insertion of an introducer. The dilator may then be removed, and the introducer passed over the guidewire into the right internal jugular vein of the patient 50. Once the introducer is placed within the right internal jugular vein, a central end portion 112 of the first tubular conduit 110 may be inserted through the introducer and advanced within the patient 50 such that the central end portion 112 of the first tubular conduit 110 passes through the superior vena cava into the right atrium of a heart 20 (e.g., the mid to upper right atrium) as depicted in FIG. 2A. Advancement of the first tubular conduit 110 into the patient 50 may be done under fluoroscopic guidance.

After the central end portion 112 of the first tubular conduit 110 has been placed within the right atrium of the heart 20, a second incision 4 (see FIG. 2B) may be made in the shoulder region of the patient 50 (e.g., adjacent the deltopectoral groove). A tunneling device may then be used to establish a subcutaneous path between the first incision 2 in the neck region of the patient 50 and the second incision 4 in the shoulder region of the patient 50. The peripheral end 114 of the first tubular conduit 110 may then be inserted into the first incision 2 and advanced along the path established by the tunneling device (i.e., the first tubular conduit 110 is tunneled) such that the first tubular conduit 110 extends from the right atrium of the heart 20 to the second incision 4 in the shoulder region of the patient 50 as shown in FIG. 2B.

Figure 2C:
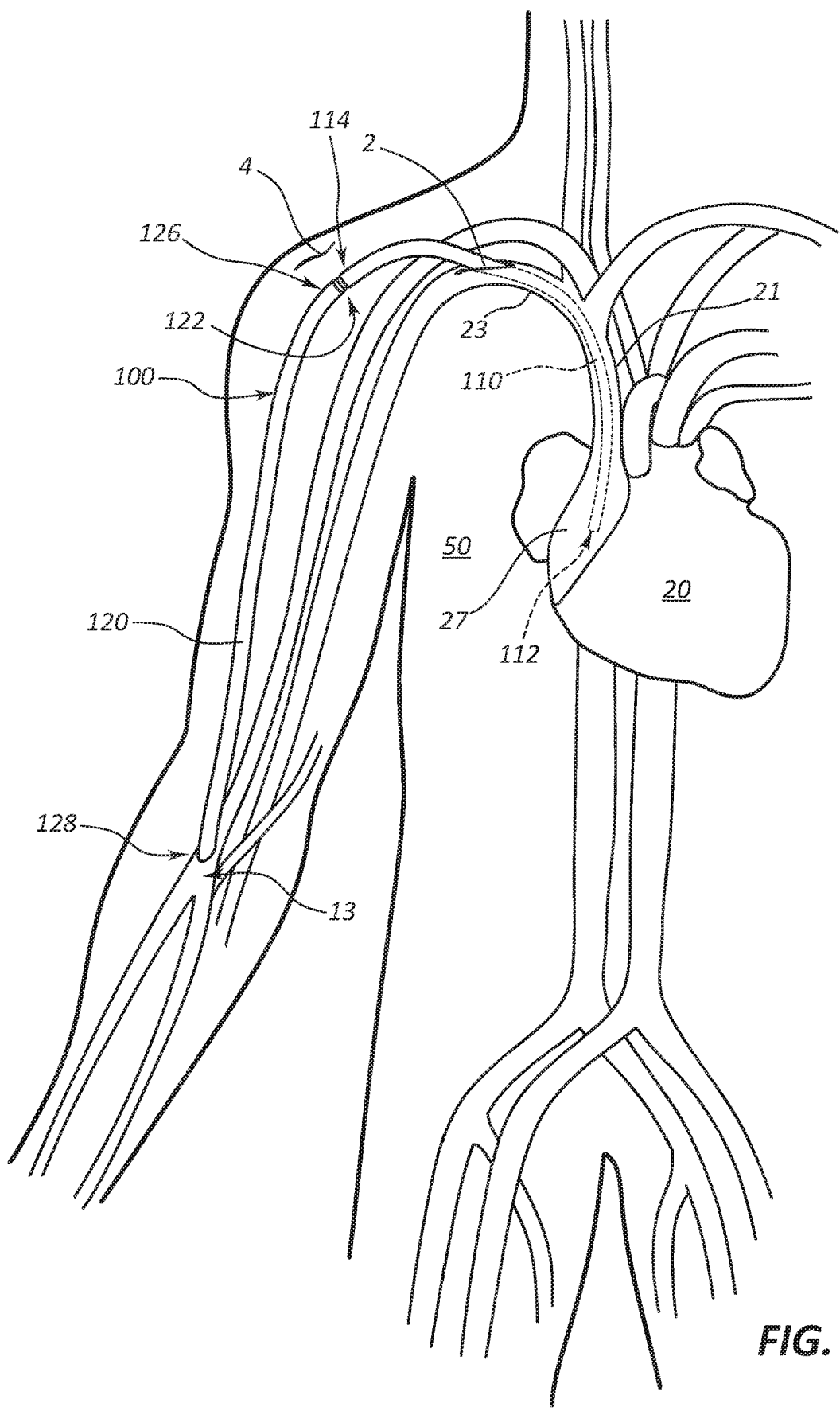
FIG. 2C depicts a second tubular conduit of the vascular access assembly of FIG. 1 that has been inserted into the patient such that the second tubular conduit extends from the incision in the shoulder region of the patient to a target site.

Once the first tubular conduit 110 has been placed such that the first tubular conduit 110 extends from the right atrium of the heart 20 to the second incision 4 in the shoulder region of the patient 50, an incision may be made at a target site 13, for example, in an artery as depicted. In some other embodiments, the target site 13 may be in an arteriovenous graft, a vein, or another suitable position. A tunneling device may then be used to establish a subcutaneous path between the second incision 4 in the shoulder region of the patient 50 to the target site 13. A peripheral end 128 of the second tubular conduit 120 may then be inserted into the second incision 4 and advanced along the path established by the tunneling device (i.e., the second tubular conduit 120 is tunneled) such that the second tubular conduit 120 extends from the second incision 4 in the shoulder region of the patient 50 to the target site 13 as shown in FIG. 2C.

With the central end portion 112 of the first tubular conduit 110 disposed within the right atrium of the heart 20 of the patient 50, the peripheral end 114 of the first tubular conduit 110 may then, if needed, be cut to the appropriate length. In other words, the first tubular conduit 110 may initially (e.g., when manufactured and inserted as described above) have a length that is longer than is needed to establish a flow path from the right atrium of the heart 20 of the patient 50 to the second incision 4 in the shoulder region of the patient 50. The first tubular conduit 110 may then be cut to proper length to facilitate coupling of the second tubular conduit 120 to the first tubular conduit 110 at the second incision 4 in the shoulder region of the patient 50. As depicted, the central end 126 of the second tubular conduit 120 may be coupled to the peripheral end 114 of the first tubular conduit 110 via the connector 122.

Similarly, in some embodiments, the second tubular conduit 120 may have an initial length that is longer than is needed to establish a flow path from the second incision 4 in the shoulder region of the patient 50 to the target site 13. In such embodiments, the central end 126 of the second tubular conduit 120 may be cut to the appropriate length once the second tubular conduit 120 has been inserted into the patient 50. In some embodiments, the connector 122 may then be attached to the newly formed central end portion of the second tubular conduit 120. In some other embodiments, no cutting of the second tubular conduit 120 may be needed.

Once the first tubular conduit 110 and the second tubular conduit 120 are the proper length, the second tubular conduit 120 may be coupled to the first tubular conduit 110, or vice versa. For example, the connector 122 at the central end 126 of the second tubular conduit 120 may be inserted into the peripheral end 114 of the first tubular conduit 110 such that the barbs or protrusions 124 of the connector 122 engage with an inner surface of the first tubular conduit 110 (see FIG. 1). Such engagement may establish a fluid-tight connection between the first tubular conduit 110 and the second tubular conduit 120. Establishment of a fluid-tight connection can be confirmed by attaching the peripheral end 128 of the second tubular conduit 120 to a syringe and advancing fluid (e.g., heparinized saline) through the system.

The peripheral end 128 of the second tubular conduit 120 may be coupled to an artery at the target site 13. For example, an incision may be made at the target site 13 and an arterial anastomosis may be performed between the peripheral end 128 of the second tubular conduit 120 and the target site 13. Coupling of a portion of the vascular access assembly 100 (e.g., the peripheral end 128 of the second tubular conduit 120) to an artery may be performed via any suitable technique. Once a flow path from the target site 13 to the heart 20 has been established as shown in FIG. 2C, the first incision 2 and the second incision 4 may be closed via any suitable technique. In this manner, the vascular access assembly 100 may, when implanted and assembled, be a fully subcutaneous surgical implant. Furthermore, the implanted and assembled vascular access assembly 100 may, as described above, be implanted without establishing a venous anastomosis.

The implanted vascular access assembly 100 may be used to facilitate vascular access. For example, in the case of hemodialysis, a practitioner may insert a first needle through the skin of the patient 50 and into the vascular access assembly 100. More particularly, the first needle may be inserted into the second tubular conduit 120. Fluid may be withdrawn from the vascular access assembly 100 and drawn into a dialysis machine that purifies the blood. The purified blood may then be returned to the patient 50 via a second needle that extends through the skin of the patient 50 and into a more central location of the second tubular conduit 120.

The steps of the procedure described above are only exemplary in nature. In other words, the vascular access assembly 100 may be implanted into the patient 50 via a procedure that deviates somewhat from the procedure described above. One of ordinary skill in the art, having the benefit of this disclosure, will also appreciate that some of the steps described above need not be performed in the order that is specified above.

An additional aspect of the disclosure relates to methods of accessing an implanted vascular access assembly 100. A practitioner may desire to access the vascular access assembly 100 so that the practitioner may clean or clear at least a portion of the vascular access assembly 100. In some embodiments, the vascular access assembly 100, or at least a portion of the vascular access assembly 100, may become occluded and/or blocked during use. For example, a blood clot or other embolus may develop within at least a portion of the vascular access assembly 100. Accordingly, the practitioner may access the vascular access assembly 100 to remove the blood clot or other embolus from within the vascular access assembly 100. In an effort to streamline the disclosure, the methods provided herein generally refer to the removal of a blood clot from the vascular access assembly 100. The provided methods, however, may also be used and/or adapted for the removal of other types of emboli from within the vascular access assembly 100 (e.g., fatty deposits, tissue growths, etc.).

Figure 3A:
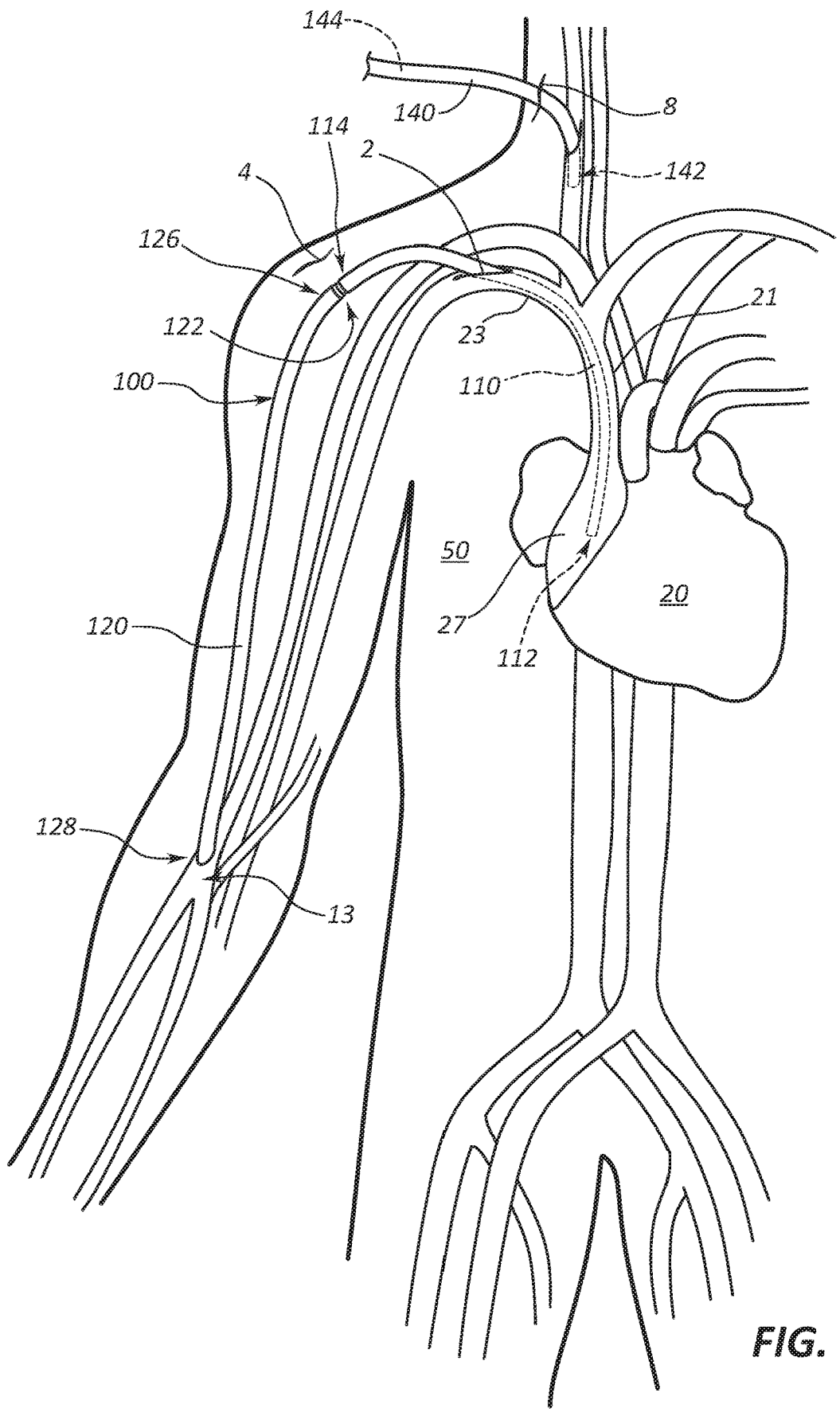
FIG. 3A depicts a catheter that has been inserted into a jugular vein of a patient.

FIG. 3A depicts a catheter 140 that has been inserted into an internal jugular vein 25 of the patient 50. The catheter 140 may be a component of a vascular access assembly declotting system. As shown, a vascular access assembly 100 is disposed in the patient 50. A practitioner may make an incision or a third incision 8 at or adjacent a neck of the patient 50. The practitioner may then dispose at least a portion of the catheter 140 through the incision 8 and into at least a portion of the jugular vein 25.

Figure 3B:
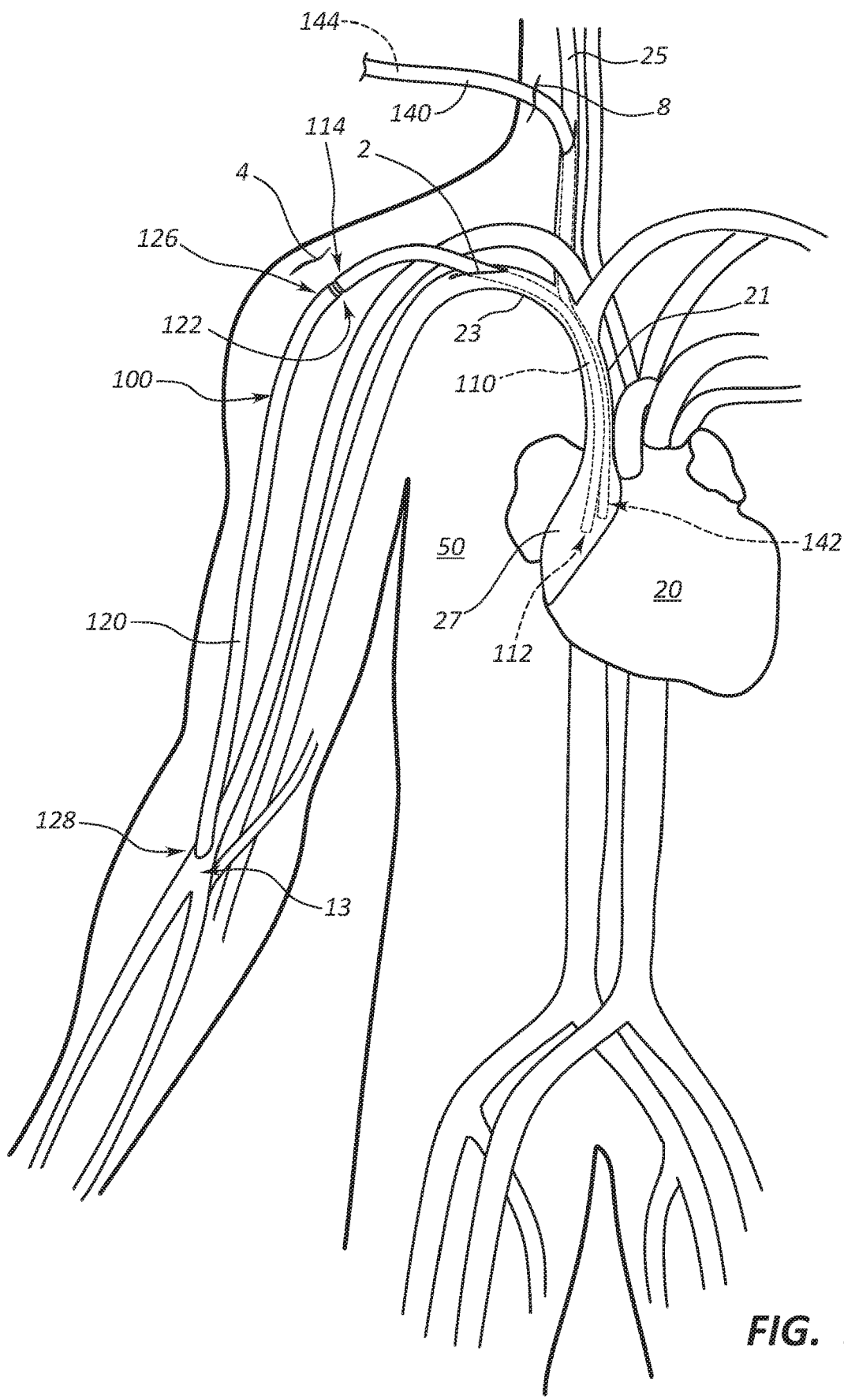
FIG. 3B depicts the catheter of FIG. 3A inserted into the patient such that a central end portion of the catheter is disposed in the right atrium of the patient.

The practitioner may then displace the catheter 140 through at least a portion of the vasculature of the patient 50 such that a central end portion 142 of the catheter 140 is displaced through the jugular vein, a brachiocephalic vein, and/or a superior vena cava, and into at least a portion of the right atrium 27 of the heart 20. As illustrated in FIG. 3B, the practitioner may displace the catheter 140 through the right internal jugular vein 25, the right brachiocephalic vein 23, and the superior vena cava 21, and into at least a portion of the right atrium 27 of the heart 20.

In some other embodiments, the practitioner may displace the catheter 140 from the left lateral side of the patient 50, for example, through the left internal jugular vein, the left brachiocephalic vein, the superior vena cava 21, and into at least a portion of the right atrium 27 of the heart 20. Due to the disposition of the first tubular conduit 110 within at least a portion of the vasculature on the right lateral side of the patient 50 (e.g., within the right brachiocephalic vein 23), access to the right atrium 27 for the catheter 140 may be less obstructed from the left lateral side of the patient 50. For example, an inside diameter of the right brachiocephalic vein 23 may be too narrow or small for passage of two elongate medical devices (e.g., the first tubular conduit 110 and the catheter 140). Accordingly, access to the right atrium 27 from the left lateral side of the patient 50 may avoid interactions or obstructions between the catheter 140 and the first tubular conduit 110 along at least a portion of a path of the catheter 140 through the vasculature to the right atrium 27.

Figure 3C:
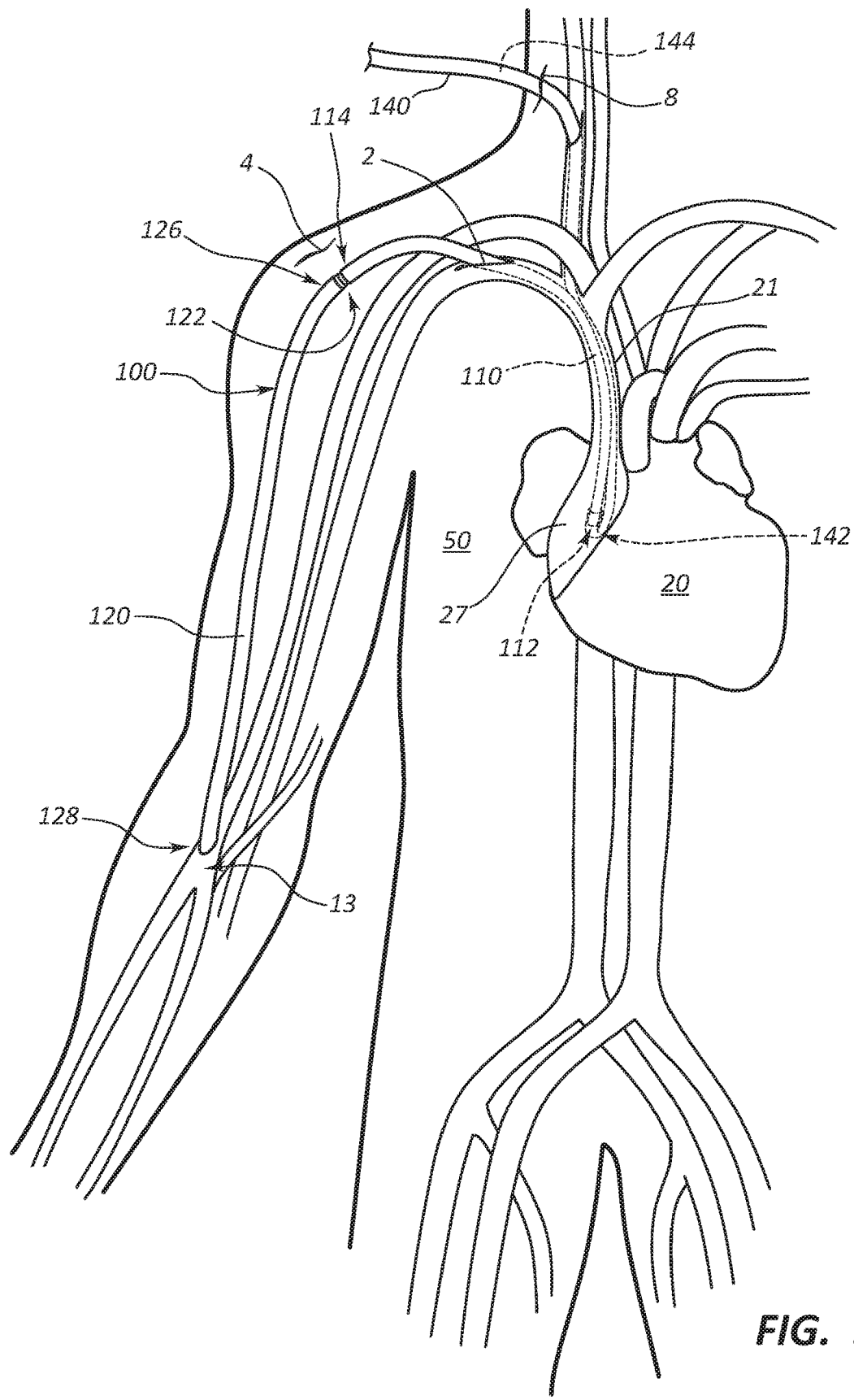
FIG. 3C depicts the central end portion of the catheter coupled to a central end portion of a first tubular conduit of a vascular access assembly.
Figures 1, 3C:
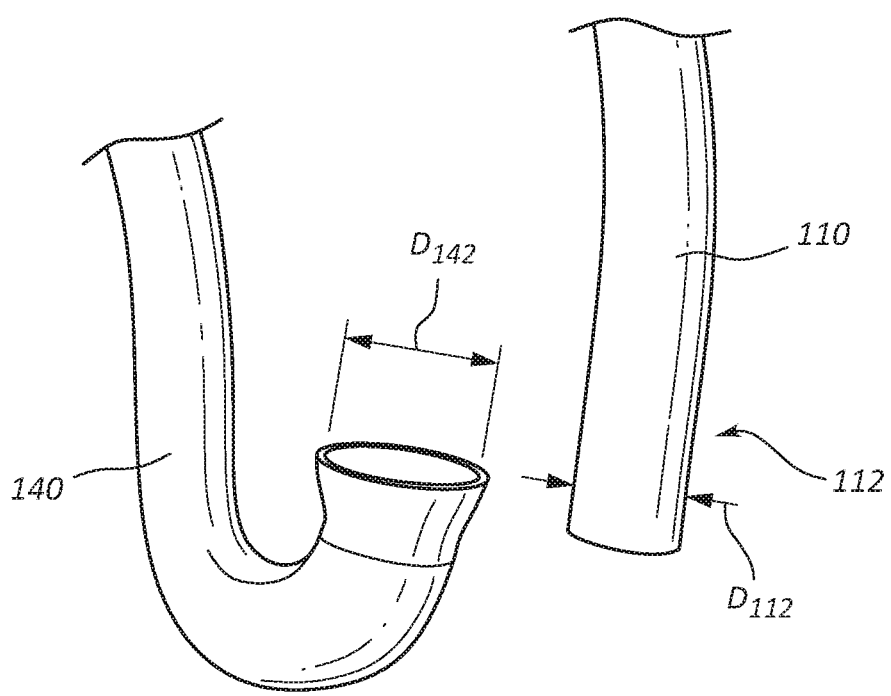

Upon disposition of the central end portion 142 of the catheter 140 within the right atrium 27, the catheter 140 may be coupled to the first tubular conduit 110 as shown in FIG. 3C. In some embodiments, the central end portion 142 of the catheter 140 may be coupled to the central end portion 112 of the first tubular conduit 110.

With reference to FIGS. 3A-3C, in certain embodiments, methods of declotting or removing a clot from the vascular access assembly 100 within the patient 50 may include inserting the central end portion 142 of the catheter 140 into the patient 50. The central end portion 142 of the catheter 140 may be displaced through at least a portion of the vasculature of the patient 50 such that the central end portion 142 of the catheter 140 is disposed within the right atrium 27 of the heart 20 of the patient 50. In certain embodiments, the central end portion 142 of the catheter 140 may be disposed within the right atrium 27 via the internal jugular vein 25 (e.g., the right internal jugular vein) as depicted in FIGS. 3A-3C. In certain other embodiments, the central end portion 142 of the catheter 140 may be disposed within the right atrium 27 via a femoral vein 47 (e.g., the right femoral vein) as described below (see, e.g., FIGS. 4A-4C).

In various embodiments, methods of declotting the vascular access assembly 100 may include coupling at least a portion of the central end portion 142 of the catheter 140 to at least a portion of a central end portion of the vascular access assembly 100 (e.g., the central end portion 112 of the first tubular conduit 110). The central end portion 142 of the catheter 140 may be coupled to the central end portion of the vascular access assembly 100 within the right atrium 27 (see, e.g., FIG. 3C).

In various embodiments, methods of declotting the vascular access assembly 100 may include evacuating a clot from within a portion of the vascular access assembly 100. The clot may be evacuated from within the portion of the vascular access assembly 100 via at least a portion of the catheter 140 (e.g., via a lumen 144 of the catheter 140). In some embodiments, the methods may include applying a suction force on the catheter 140 (e.g., on the lumen 144 of the catheter 140) such that at least a portion of the suction force may be applied on the vascular access assembly 100 (e.g., on a lumen of the first tubular conduit 110) to evacuate the clot. For example, a vacuum source may be coupled to or placed in fluid communication with a peripheral end of the catheter 140. In some embodiments, the vacuum source may be a component of the vascular access assembly declotting system. The vacuum source may be activated (e.g., by the practitioner) such that the suction force is applied on the catheter 140 and/or the vascular access assembly 100. Other methods of applying a suction force on the clot via the catheter 140 are also within the scope of this disclosure.

In some embodiments, methods of declotting the vascular access assembly 100 may further include flushing (e.g., with a fluid such as a saline solution) a portion of the vascular access assembly 100. The flushing may act to displace or loosen the clot or at least a portion of the clot such that the clot may be displaced from within the vascular access assembly 100 to the lumen 144 of the catheter 140.

Methods of declotting the vascular access assembly 100 may also include displacing the clot or at least a portion of the clot from within the vascular access assembly 100 to the lumen 144 of the catheter 140 and grinding or macerating at least a portion of the clot (e.g., with a macerator) as the clot is displaced from within the vascular access assembly 100 to the lumen 144 of the catheter 140. Grinding or macerating of the clot may aid or ease displacement of the clot through the lumen 144 of the catheter 140. Embodiments of catheters including a macerator are discussed in further detail below in reference to FIG. 5.

Figures 2, 3C:
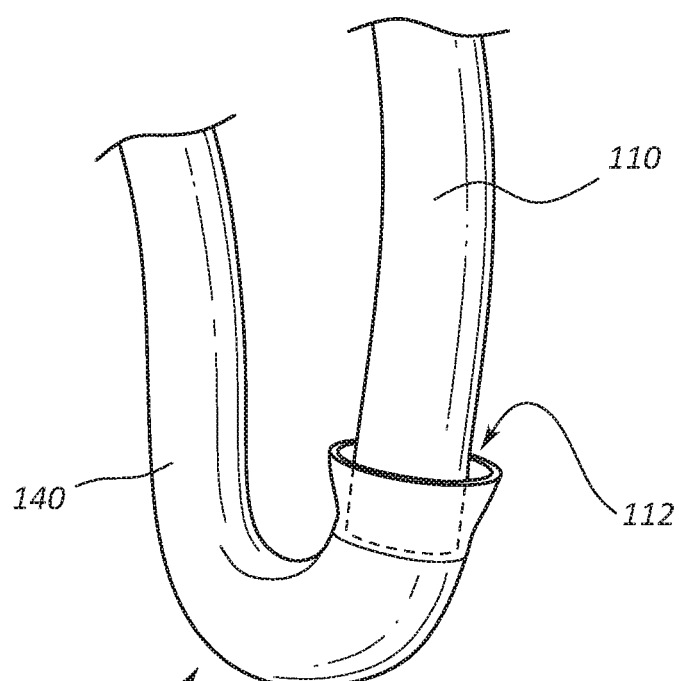

FIG. 3C-1 depicts the central end portion 142 of the catheter 140 and the central end portion 112 of the first tubular conduit 110 in a decoupled configuration and FIG. 3C-2 depicts the central end portion 142 of the catheter 140 and the central end portion 112 of the first tubular conduit 110 in a coupled configuration. As illustrated, at least a portion of the central end portion 142 of the catheter 140 may be funnel shaped. The funnel shape may aid in the coupling of the catheter 140 to the first tubular conduit 110. For example, an inside surface of the funnel-shaped central end portion 142 may guide the central end portion 112 of the first tubular conduit 110 into at least a portion of the catheter 140 such that the first tubular conduit 110 and the catheter 140 may be coupled to each other.

With reference to FIG. 3C-2, an internal diameter $D_{142}$ of at least a portion of the central end portion 142 of the catheter 140 can be greater than an external diameter $D_{112}$ of at least a portion of the central end portion 112 of the first tubular conduit 110. Accordingly, at least a portion of the central end portion 142 of the catheter 140 may be displaceable around at least a portion of the central end portion 112 of the first tubular conduit 110. In various embodiments, the coupling of the central end portion 142 of the catheter 140 to the central end portion 112 of the first tubular conduit 110 can form a substantially fluid-tight seal. For example, the catheter 140 may be coupled to the first tubular conduit 110 such that the contents of the catheter 140 and/or the first tubular conduit 110 (e.g., a portion of a clot) do not leak into the right atrium 27.

As shown in FIGS. 3C-1 and 3C-2, at least a portion of the central end portion 142 of the catheter 140 may be substantially J shaped. In some embodiments, the central end portion 142 of the catheter 140 may have a low-profile state and a deployed state. The low-profile state may be substantially linear such that the central end portion 142 of the catheter 140 may be displaced through the vasculature of the patient 50 more easily and/or such that the central end portion 142 of the catheter 140 is atraumatic. For example, when in the low-profile state, the central end portion 142 of the catheter 140 may be configured to avoid or limit damaging the vasculature. The deployed state may be substantially J shaped. For example, upon disposition of the central end portion 142 of the catheter 140 within the atrium, the central end portion 142 may transition between the low-profile state (e.g., a low-profile configuration) and the deployed state (e.g., the J-shaped configuration).

In certain embodiments, the practitioner may actuate the catheter 140 such that the central end portion 142 of the catheter 140 transitions from the low-profile state to the deployed state. For example, the practitioner may pull on a wire that results in bending or curving of at least a portion of the central end portion 142. When in the deployed state, the central end portion 142 may be configured to be displaced over and/or around at least a portion of the central end portion 112 of the first tubular conduit 110 such that the catheter 140 may be coupled to the first tubular conduit 110. For example, the practitioner may displace the catheter 140 peripherally relative to the heart 20 and dispose the central end portion 142 of the catheter 140 around and/or over at least a portion of the central end portion 112 of the first tubular conduit 110.

In various embodiments, the central end portion 142 of the catheter 140 may include a purse string mechanism or an iris mechanism (not shown). The purse string mechanism may be disposed at or adjacent a central end of the central end portion 142 of the catheter 140. The purse string mechanism may include a suture or wire that is disposed around a circumference of the central end portion 142 of the catheter 140. The purse string mechanism may be configured to transition the central end portion 142 of the catheter 140 between an open state and a closed state. When in the closed state, the central end portion 142 of the catheter 140 may be configured to form a seal between an inside surface of at least a portion of the central end portion 142 of the catheter 140 and at least a portion of an outside surface of the central end portion 112 of the first tubular conduit 110.

As discussed above, the vascular access assembly 100 can include a first tubular conduit 110 having a central end portion 112 disposed within the heart 20 of the patient 50. The vascular access assembly 100 can further include a second tubular conduit 120 having a peripheral end 128 coupled to a vessel of the patient 50. Furthermore, a peripheral end 114 of the first tubular conduit 110 may be releasably coupled (e.g., by an adaptor 122) to a central end 126 of the second tubular conduit 120. Accordingly, a flow path can extend from the vessel to the heart 20 via the first and second tubular conduits 110, 120. The flow path may extend from a brachial artery or an arteriovenous graft to the right atrium 27.

In some embodiments, methods of declotting the vascular access assembly 100 may further include decoupling the first tubular conduit 110 and the second tubular conduit 120, for example, at the adaptor 122. The practitioner may then couple a flushing mechanism (not shown) to the peripheral end 114 of the first tubular conduit 110. The flushing mechanism may be a component of the vascular access assembly declotting system. In certain embodiments, the flushing mechanism may include a flushing catheter, wherein a peripheral end portion of the flushing catheter is in fluid communication with a fluid source (e.g., a source of a saline solution or another suitable fluid). Upon coupling of the flushing mechanism and the first tubular conduit 110, the practitioner may displace a fluid through at least a portion of the flushing mechanism and through at least a portion of the first tubular conduit 110. Stated another way, the practitioner may flush the first tubular conduit 110 such that a clot is displaced from within the first tubular conduit 110 to the lumen 144 of the catheter 140.

In certain embodiments, methods of declotting or removing a clot from the vascular access assembly 100 within the patient 50 can include: accessing a jugular vein of the patient 50, inserting the central end portion 142 of the catheter 140 into the jugular vein, displacing the catheter 140 such that the central end portion 142 of the catheter 140 is disposed within the right atrium 27 of the heart 20 of the patient 50, coupling the central end portion 142 of the catheter 140 to the central end portion 112 of the vascular access assembly 100 disposed within the right atrium 27, and/or evacuating the clot from within a portion of the vascular access assembly 100 via the catheter 140. The methods may further include evacuating or sucking the clot from within at least a portion of the vascular access assembly 100 and through the catheter 140 to evacuate the clot from within the vascular access assembly 100.

Displacing the catheter 140 such that the central end portion 142 of the catheter 140 is disposed within the right atrium 27 may further include displacing the central end portion 142 of the catheter 140 through at least a portion of each of the right internal jugular vein 25, the right brachiocephalic vein 23, and/or the superior vena cava 21 of the patient 50. Other methods of accessing the right atrium 27 are also within the scope of this disclosure (e.g., via the vasculature of the left lateral side of the patient 50 as discussed above or via a femoral vein as described in further detail below).

Figures 3, 3C:
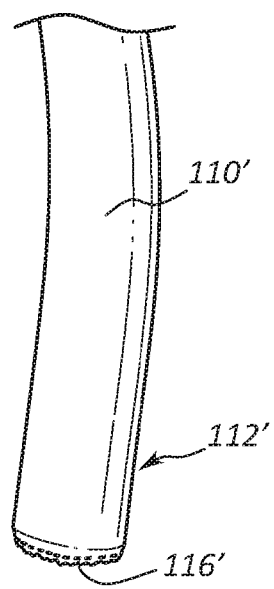

FIG. 3C-3 depicts a central end portion 112' of a first tubular conduit 110'. As shown, the central end portion 112' of the first tubular conduit 110' may include a purse string mechanism 116' or an iris mechanism. The purse string mechanism 116' may be disposed at or adjacent a central end of the central end portion 112' of the first tubular conduit 110'. Analogous to the discussion above, the purse string mechanism 116' may include a suture or wire that is disposed around a circumference of the central end portion 112' of the first tubular conduit 110'. The purse string mechanism 116' may be configured to transition the central end portion 112' of the first tubular conduit 110' between an open state and a closed state. When in the closed state, the central end portion 112' of the first tubular conduit 110' may be configured to form a seal at or adjacent the central end portion 112' of the first tubular conduit 110'.

In some embodiments, the purse string mechanism 116' may utilized to close the central end portion 112' of the first tubular conduit 110' prior to removal of the first tubular conduit 110'. For instance, a practitioner may desire to remove and replace a tubular conduit from an implanted assembly, due to clotting of that conduit, for example. Use of a purse string, such as purse string mechanism 116' may prevent a clot from exiting the conduit while that conduit is being removed. Thus, in some instances, a practitioner may close the end of the conduit via a purse string or other mechanism, prior to removing the conduit from the patient's body. A replacement conduit may then be introduced to replace the withdrawn conduit.

In some embodiments, methods of declotting a vascular access assembly may include decoupling the first tubular conduit 110' and a second tubular conduit (e.g., at an adaptor) and the method may utilize a vacuum. The practitioner may then couple a vacuum source to a peripheral end of the first tubular conduit 110'. In certain embodiments, the vacuum source may be coupled to the first tubular conduit 110' via a vacuum catheter. The practitioner may also transition the central end portion 112' of the first tubular conduit 110' to the closed state, for example, by actuating the purse string mechanism 116'. In some embodiments, the vacuum source and/or the vacuum catheter may be components of the vascular access assembly declotting system.

The vacuum source may be activated (e.g., by the practitioner) such that a suction force is applied on the first tubular conduit 110' and a clot disposed within the first tubular conduit 110' can be displaced from within, evacuated from, or sucked out of the first tubular conduit 110'. Disposition of the purse string mechanism 116' and/or the central end portion 112' of the first tubular conduit 110' in the closed state may limit or prevent the clot, or a portion of the clot, from exiting the first tubular conduit 110' at the central end portion 112'. Accordingly, the clot may be limited or prevented from entering or being lost into the vena cava and/or the heart of the patient.

FIGS. 4A-4C-2 depict an embodiment of a vascular access assembly 200 that resembles the vascular access assembly 100 described above in certain respects. Accordingly, like features are designated with like reference numerals, with the leading digits incremented to "2." For example, the embodiment depicted in FIGS. 4A-4C-2 includes a first tubular conduit 210 that may, in some respects, resemble the first tubular conduit 110 of FIGS. 1-3C-2. Relevant disclosure set forth above regarding similarly identified features thus may not be repeated hereafter. Moreover, specific features of the vascular access assembly 100 and related components shown in FIGS. 1-3C-2 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the vascular access assembly 200 and related components depicted in FIGS. 4A-4C-2. Any suitable combination of the features, and variations of the same, described with respect to the vascular access assembly 100 and related components illustrated in FIGS. 1-3C-2 can be employed with the vascular access assembly 200 and related components of FIGS. 4A-4C-2, and vice versa. This pattern of disclosure applies equally to further embodiments depicted in subsequent figures and described hereafter, wherein the leading digits may be further incremented.

Figure 4A:
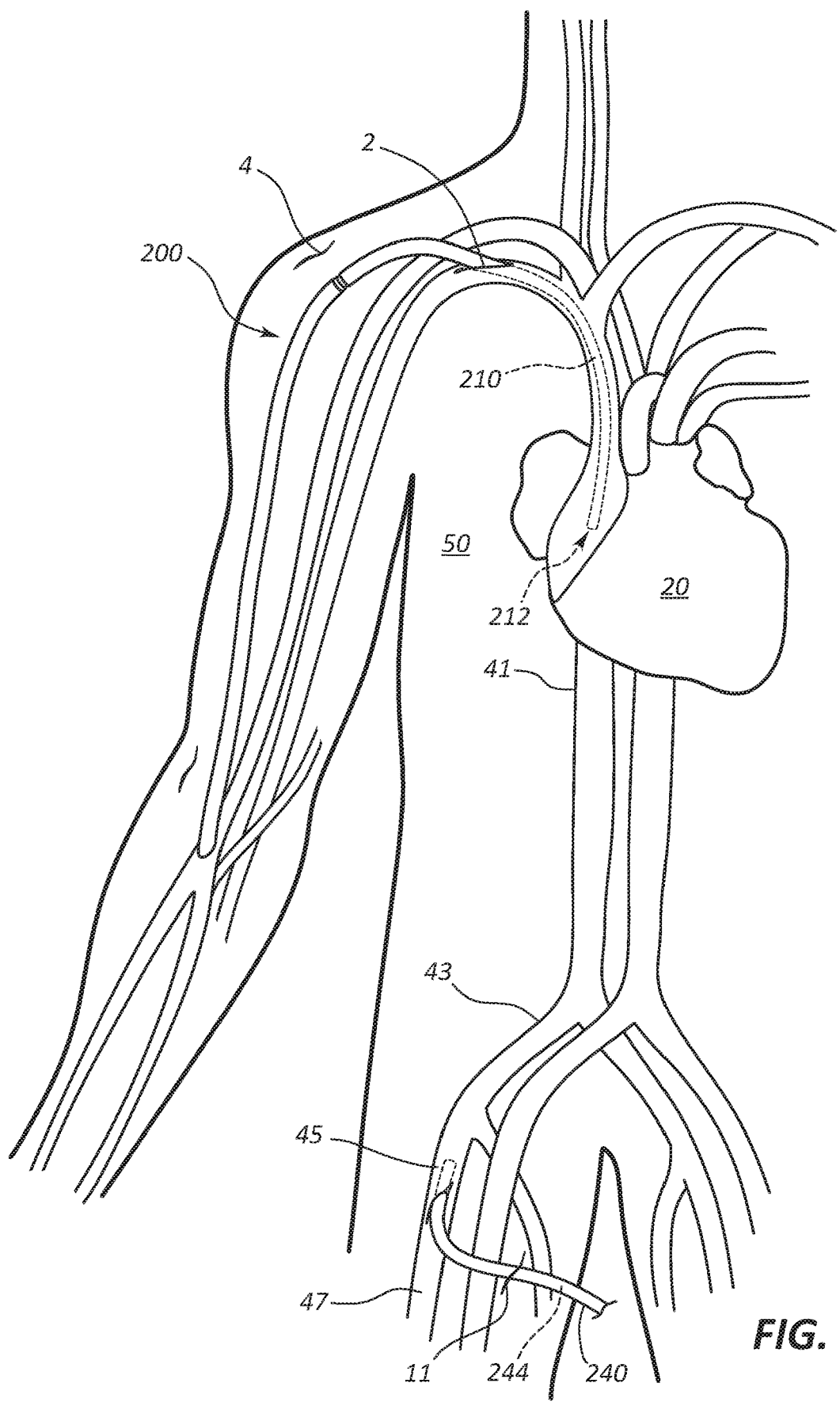
FIG. 4A depicts a catheter that has been inserted into a femoral vein of a patient.

FIG. 4A depicts a catheter 240 that has been inserted into a femoral vein 47 of the patient 50. As shown, a vascular access assembly 200 is disposed in the patient 50. A practitioner may make an incision or a fourth incision 11 at or adjacent a thigh or an upper leg of the patient 50. The practitioner may then dispose at least a portion of the catheter 240 through the incision 11 and into at least a portion of the femoral vein 47.

Figure 4B:
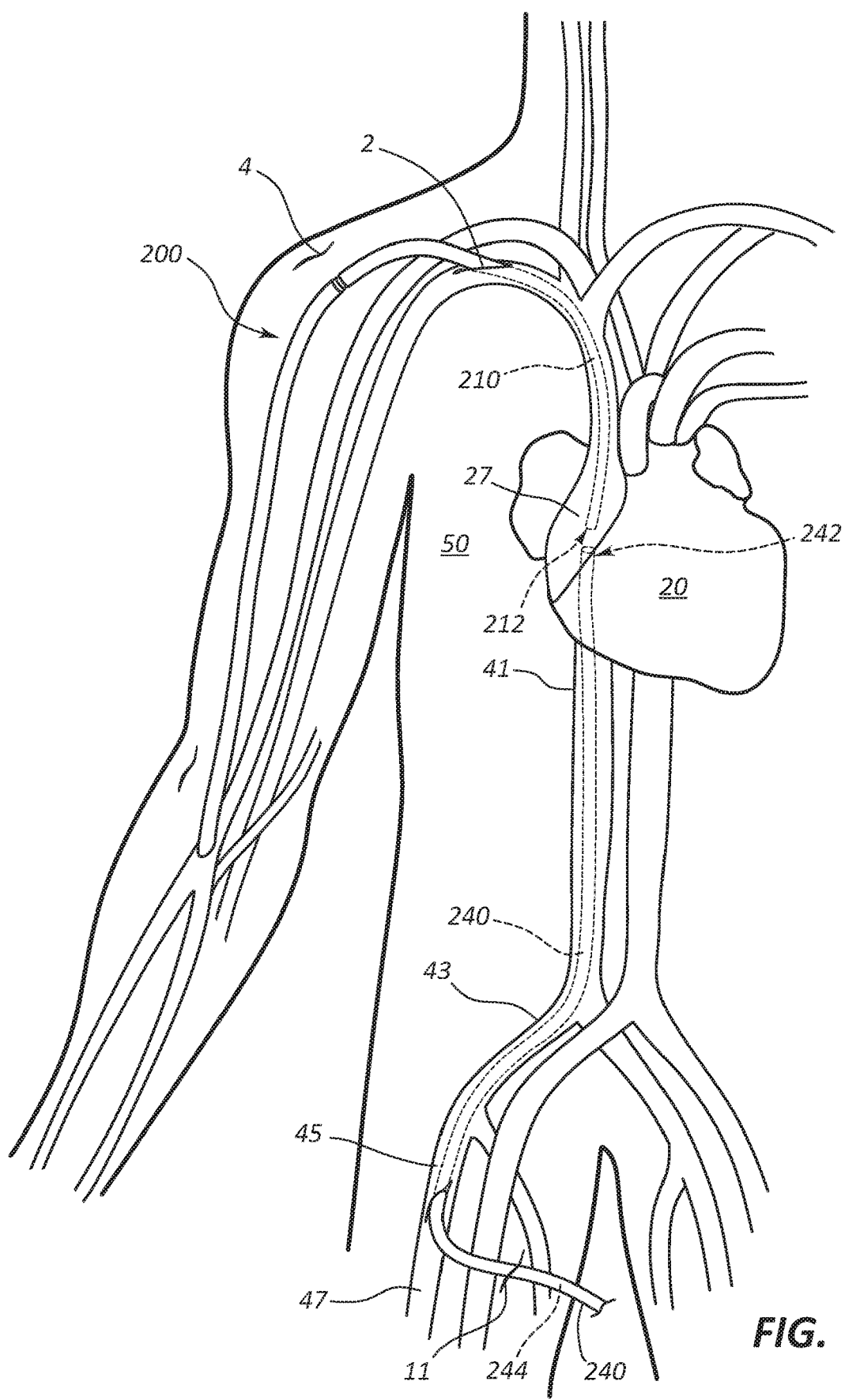
FIG. 4B depicts the catheter of FIG. 4A inserted into the patient such that a central end portion of the catheter is disposed in the right atrium of the patient.

The practitioner may then displace the catheter 240 through at least a portion of the vasculature of the patient 50 such that a central end portion 242 of the catheter 240 is displaced through a femoral vein, an external iliac vein, a common iliac vein, and/or an inferior vena cava, and into at least a portion of the right atrium 27 of the heart 20. As discuss above in reference to jugular access, femoral access may also be performed through either the right lateral side or the left lateral side of the patient 50. As illustrated in FIG. 4B, the practitioner may displace the catheter 240 through the right femoral vein 47, the right external iliac vein 45, the right common iliac vein 43, and the inferior vena cava 41, and into at least a portion of the right atrium 27 of the heart 20.

Figure 4C:
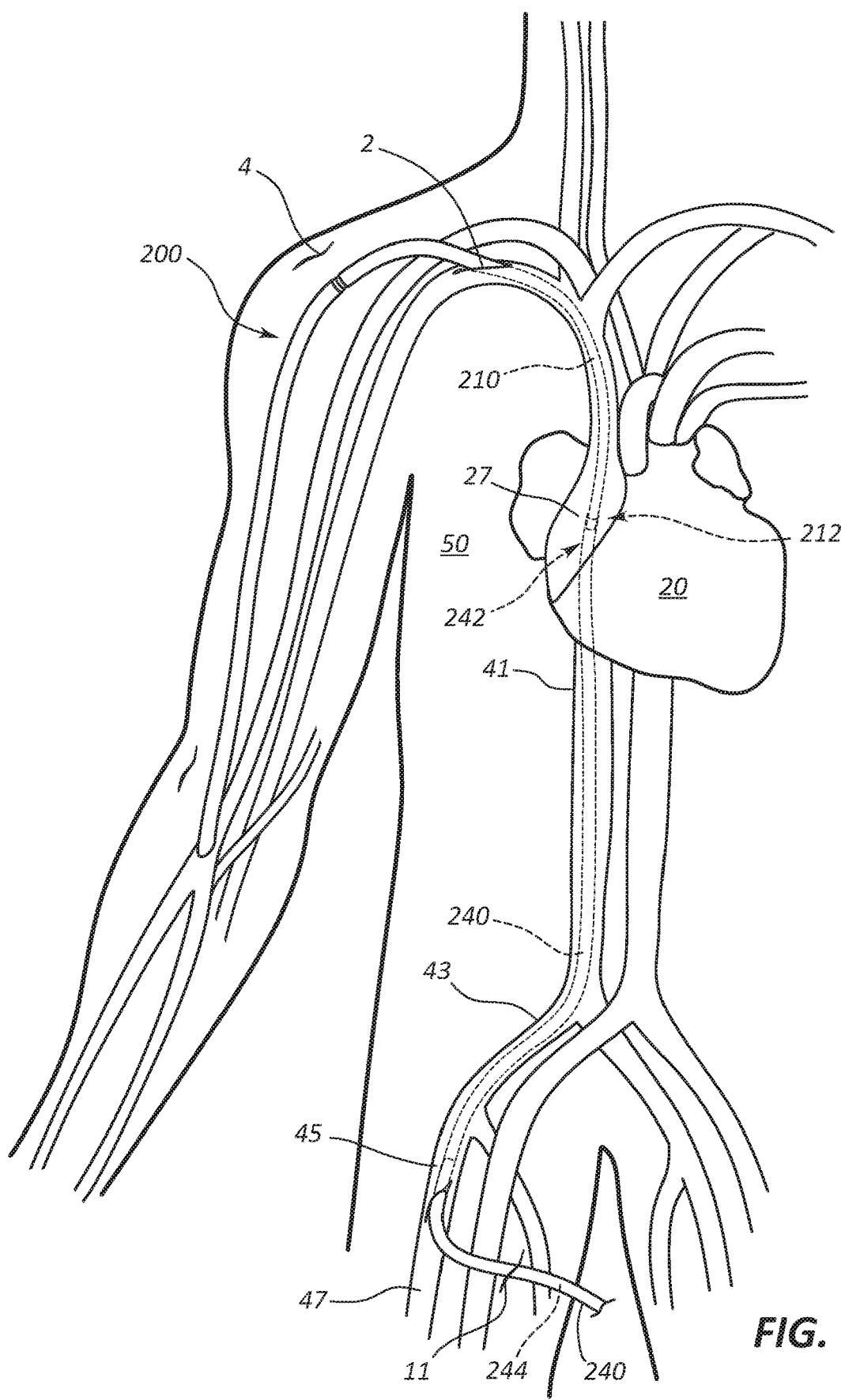
FIG. 4C depicts the central end portion of the catheter coupled to a central end portion of a first tubular conduit of a vascular access assembly.
Figures 1, 4C:
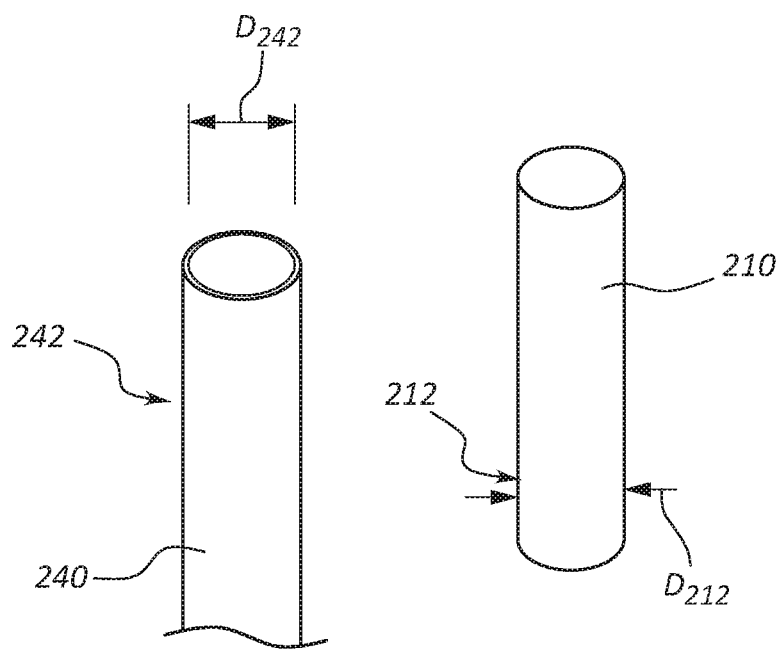
Figures 2, 4C:
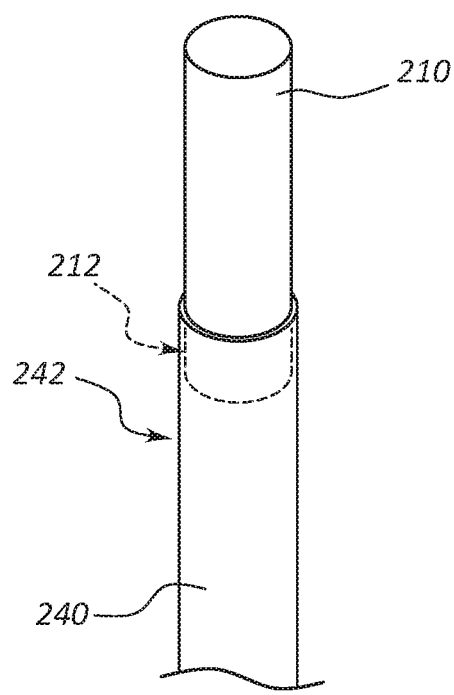

Upon disposition of the central end portion 242 of the catheter 240 within the right atrium 27, the catheter 240 may be coupled to the first tubular conduit 210 as shown in FIG. 4C. In some embodiments, the central end portion 242 of the catheter 240 may be coupled to a central end portion 212 of the first tubular conduit 210.

In various embodiments, methods of declotting the vascular access assembly 200 may include coupling at least a portion of the central end portion 242 of the catheter 240 to at least a portion of a central end portion of the vascular access assembly 200 (i.e., the central end portion 212 of the first tubular conduit 210). The central end portion 242 of the catheter 240 may be coupled to the central end portion of the vascular access assembly 200 within the right atrium 27 (see, e.g., FIG. 4C).

In various embodiments, methods of declotting the vascular access assembly 200 may include evacuating a clot from within a portion of the vascular access assembly 200. The clot may be evacuated from within the portion of the vascular access assembly 200 via at least a portion of the catheter 240 (e.g., via a lumen 244 of the catheter 240). As discussed above in reference to catheter 140, the methods may include applying a suction force on the catheter 240 such that at least a portion of the suction force may be applied on the vascular access assembly 200 (e.g., on a lumen of the first tubular conduit 210) to evacuate the clot. Furthermore, methods of declotting the vascular access assembly 200 may also include flushing (e.g., with a fluid such as a saline solution) a portion of the vascular access assembly 200.

FIG. 4C-1 depicts the central end portion 242 of the catheter 240 and the central end portion 212 of the first tubular conduit 210 in a decoupled configuration and FIG. 4C-2 depicts the central end portion 242 of the catheter 240 and the central end portion 212 of the first tubular conduit 210 in a coupled configuration. With reference to FIG. 4C-1, an internal diameter $D_{242}$ of at least a portion of the central end portion 242 of the catheter 240 can be greater than an external diameter $D_{212}$ of at least a portion the central end portion 212 of the first tubular conduit 210 (e.g., the central end portion of the vascular access assembly 200). Accordingly, with reference to FIG. 4C-2, at least a portion of the central end portion 242 of the catheter 240 may be displaceable around at least a portion of the central end portion 212 of the first tubular conduit 210.

As shown in FIG. 4C-1, at least a portion of the central end portion 242 of the catheter 240 may be substantially linear. The practitioner may displace the catheter 240 centrally relative to the heart 20 and dispose the central end portion 242 of the catheter 240 around and/or over at least a portion of the central end portion 212 of the first tubular conduit 210 (e.g., to form a seal between the catheter 240 and the first tubular conduit 210). Other embodiments of the catheter 240 and/or the central end portion 242 of the catheter 240, as disclosed herein, may be used in methods of femoral vein access to the right atrium 27. For example, the catheter 240 may include a purse string mechanism, as described above, such that the catheter 240 may form a seal between an inside surface of at least a portion of the central end portion 242 of the catheter 240 and at least a portion of an outside surface of the central end portion 212 of the first tubular conduit 210 when in the closed state.

In certain embodiments, methods of declotting or removing a clot from the vascular access assembly 200 within the patient 50 can include: accessing the femoral vein 47 of the patient 50, inserting the central end portion 242 of the catheter 240 into at least a portion of the femoral vein 47, displacing the catheter 240 such that the central end portion 242 of the catheter 240 is disposed within the right atrium 27 of the heart 20 of the patient 50, coupling the central end portion 242 of the catheter 240 to the central end portion 212 of the first tubular conduit 210 (i.e., the central end portion of the vascular access assembly 200) disposed within the right atrium 27, and/or evacuating the clot from within a portion of the vascular access assembly 200 via the catheter 240. In some embodiments, the methods may further include sucking the clot (e.g., using a vacuum mechanism) from within the vascular access assembly 200 and through the catheter 240 to evacuate the clot from within the vascular access assembly 200.

Displacing the catheter 240 such that the central end portion 242 of the catheter 240 is disposed within at least a portion of the right atrium 27 may include displacing the central end portion 242 of the catheter 240 through each of the femoral vein 47, the external iliac vein 45, the common iliac vein 43, and/or the inferior vena cava 41 of the patient 50. As discussed above, other methods of accessing the right atrium 27 are also within the scope of this disclosure.

Figure 5:
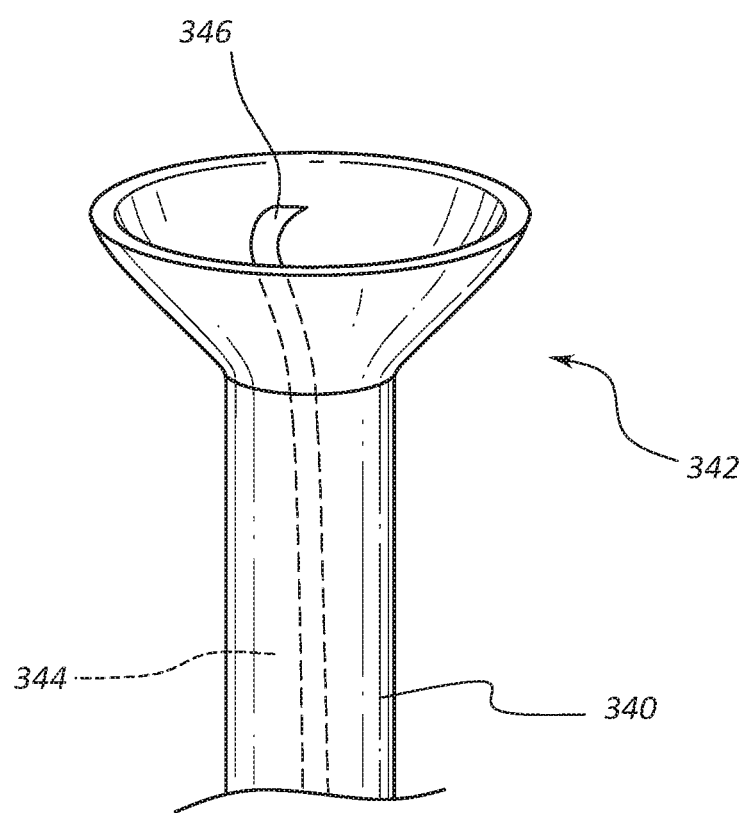
FIG. 5 is a perspective view of an embodiment of a central end portion of a catheter.

FIG. 5 illustrates a central end portion 342 of a catheter 340. The central end portion 342 of the catheter 340 may be funnel shaped. Furthermore, the catheter 340 can include a macerator 346 coupled to or disposed within at least a portion of the catheter 340. As depicted, at least a portion of the macerator 346 may be disposed at or adjacent the central end portion 342 of the catheter 340. As discussed above, a practitioner may actuate the macerator 346 such that the macerator 346 may grind or macerate a clot as the clot passes from within the vascular access assembly to the catheter 340 or a lumen 344 of the catheter 340. The grinding or macerating of the clot may aid or ease displacement of the clot through the catheter 340 or the lumen 344 of the catheter 340.

In another method of declotting a conduit, a practitioner may advance a balloon through a clotted conduit from a peripheral position toward a central position. For example, with reference to the embodiment of FIG. 1, in some instances a clot may be disposed in a portion of the vascular access assembly 100, such as within the first tubular conduit 110. A practitioner may decouple the peripheral end 114 of the first tubular conduit 110 and advance a low-profile balloon through the first tubular conduit 110 toward the central end portion 112 of the first tubular conduit 110. The balloon may be advanced in a low-profile, deflated configuration and may traverse the clot without displacing the clot in the central direction. The balloon may then be inflated and withdrawn in the peripheral direction. The inflated balloon may then be used to pull the clot in the peripheral direction and out of the peripheral end 114 of the first tubular conduit 114. Methods utilizing balloons may be utilized in any of the systems, and any of the locations within the body, described herein in connection with other embodiments or examples.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:
1. A method of declotting a vascular access assembly within a patient, the method comprising:
   inserting a central end portion of a catheter into the patient such that the central end portion of the catheter is disposed within the vasculature of the patient;

coupling the central end portion of the catheter to a central end portion of a vascular access assembly disposed within the vasculature of the patient,
wherein the vascular access assembly is completely disposed within the patient, and
wherein the coupling occurs within the vasculature of the patient; and
evacuating a clot from within a portion of the vascular access assembly via the catheter.

2. The method of claim 1, further comprising:
applying a suction force on the catheter such that a portion of the suction force is applied on the vascular access assembly to evacuate the clot.

3. The method of claim 1, further comprising:
flushing a portion of the vascular access assembly such that the clot is displaced from within the vascular access assembly to a lumen of the catheter.

4. The method of claim 1, further comprising:
displacing the clot from within the vascular access assembly to a lumen of the catheter; and
macerating a portion of the clot as the clot is displaced from within the vascular access assembly to the lumen of the catheter.

5. The method of claim 1, wherein the central end portion of the catheter is disposed within the right atrium via a jugular vein.

6. The method of claim 1, wherein the central end portion of the catheter is disposed within the right atrium via a femoral vein.

7. The method of claim 1, wherein an internal diameter of a portion of the central end portion of the catheter is greater than an external diameter of a portion of the central end portion of the vascular access assembly such that the portion of the central end portion of the catheter is displaceable around the portion of the central end portion of the vascular access assembly.

8. The method of claim 1, wherein the coupling of the central end portion of the catheter to the central end portion of the vascular access assembly forms a substantially fluid-tight seal.

9. The method of claim 1, wherein the central end portion of the catheter is substantially J shaped.

10. The method of claim 1, wherein the central end portion of the catheter is substantially funnel shaped.

11. The method of claim 1, wherein the central end portion of the catheter comprises a purse string mechanism such that the central end portion of the catheter is transitionable between an open state and a closed state and wherein the central end portion of the catheter is configured to form a seal between an inside surface of the central end portion of the catheter and an outside surface of the central end portion of the vascular access assembly when in the closed state.

12. The method of claim 1, wherein the vascular access assembly comprises:
a first tubular conduit having a central end portion disposed within a heart of the patient; and
a second tubular conduit having a peripheral end coupled to a vessel of the patient, wherein a peripheral end of the first tubular conduit is releasably coupled to a central end portion of the second tubular conduit such that a flow path extends from the vessel to the heart via the first and second tubular conduits.

13. The method of claim 12, wherein the vascular access assembly further comprises an adaptor for releasably coupling the first tubular conduit to the second tubular conduit.

14. The method of claim 13, further comprising:
decoupling the first tubular conduit and the second tubular conduit at the adaptor;
coupling a flushing mechanism to the peripheral end of the first tubular conduit; and
flushing the first tubular conduit such that the clot is displaced from within the first tubular conduit to a lumen of the catheter.

15. A method of removing a clot from a vascular access assembly within a patient, the method comprising:
accessing an internal jugular vein of the patient;
inserting a central end portion of a catheter into the internal jugular vein;
displacing the catheter such that the central end portion of the catheter is disposed within a vena cava or right atrium of a heart of the patient;
coupling the central end portion of the catheter to a central end portion of a vascular access assembly disposed within the vena cava or right atrium,
wherein the vascular access assembly is a fully subcutaneous implant, and
wherein the coupling occurs within the vena cava or right atrium; and
evacuating a clot from within a portion of the vascular access assembly via the catheter.

16. The method of claim 15, wherein displacing the catheter such that the central end portion of the catheter is disposed within the vena cava or right atrium comprises displacing the central end portion of the catheter through the internal jugular vein, a brachiocephalic vein, and a superior vena cava of the patient.

17. The method of claim 16, wherein the central end portion of the catheter is substantially J shaped such that the central end portion of the catheter is disposable around the central end portion of the vascular access assembly.

18. The method of claim 15, further comprising:
sucking the clot from within the vascular access assembly and through the catheter to evacuate the clot from within the vascular access assembly.

19. A method of removing a clot from a vascular access assembly within a patient, the method comprising:
accessing a femoral vein of the patient;
inserting a central end portion of a catheter into the femoral vein;
displacing the catheter such that the central end portion of the catheter is disposed within a vena cava or right atrium of a heart of the patient;
coupling the central end portion of the catheter to a central end portion of a vascular access assembly disposed within the vena cava or right atrium,
wherein the vascular access assembly is a fully subcutaneous implant, and
wherein the coupling occurs within the vena cava or right atrium; and
evacuating a clot from within a portion of the vascular access assembly via the catheter.

20. The method of claim 19, wherein displacing the catheter such that the central end portion of the catheter is disposed within the vena cava or right atrium comprises displacing the central end portion of the catheter through the femoral vein, an external iliac vein, a common iliac vein, and an inferior vena cava of the patient.

* * * * *